United States Patent
Kennedy

[19]

[11] Patent Number: 6,165,445
[45] Date of Patent: *Dec. 26, 2000

[54] PHARMACEUTICAL COMPOSITIONS CONTAINING ALKYLARYL POLYETHER ALCOHOL POLYMER

[75] Inventor: Thomas P. Kennedy, Richmond, Va.

[73] Assignee: Charlotte-Mecklenburg Hospital Authority, Charlotte, N.C.

[*] Notice: This patent issued on a continued prosecution application filed under 37 CFR 1.53(d), and is subject to the twenty year patent term provisions of 35 U.S.C. 154(a)(2).

[21] Appl. No.: 09/210,032

[22] Filed: Dec. 11, 1998

Related U.S. Application Data

[60] Division of application No. 08/638,893, Apr. 25, 1996, Pat. No. 5,849,263, which is a continuation-in-part of application No. 08/299,316, Aug. 31, 1994, Pat. No. 5,512,270, which is a continuation-in-part of application No. 08/039,732, Mar. 30, 1993, abandoned.

[51] Int. Cl.$^7$ .................. A61K 9/12; A61K 31/765

[52] U.S. Cl. .................................................. 424/45

[58] Field of Search .................. 424/45, 78.05, 424/78.06, 78.08, 78.37; 514/179, 885, 887

[56] References Cited

U.S. PATENT DOCUMENTS

| | | | |
|---|---|---|---|
| 2,454,541 | 11/1948 | Bock et al. | |
| 3,272,700 | 9/1966 | Shupe | 514/535 |
| 3,663,230 | 5/1972 | Sato et al. | |

(List continued on next page.)

FOREIGN PATENT DOCUMENTS

| | | |
|---|---|---|
| 0571670 | 12/1993 | European Pat. Off. |
| 0780127 | 6/1997 | European Pat. Off. |
| WO9422425 | 10/1994 | WIPO |
| WO9511669 | 5/1995 | WIPO |
| WO9630028 | 10/1996 | WIPO |

OTHER PUBLICATIONS

Harold N. Glassman, Hemolytic Activity Of Some Nonionic Surface–Active Agents, *Science*, vol. III, Jun. 23, 1950, pp. 688–689.

Oliver H. Lowry, Nira J. Rosebaugh, A Lewis Farr and Rose J. Randall, Protein Measurement With The Folin Phenol Reagent, *Journal Of Biological Chemistry*, vol. 193, 1951, pp. 265–275.

M. V. Pimm and R.W. Baldwin, Influence Of ICRF 159 and Triton WR 1339 On Metastases Of A Rat Epithelioma, *The British Journal Of Cancer*, vol. 31, No. 1, Jan. 1975, pp. 62–67.

Kunihisa Hashimoto, Senji Miura and Chigashi Suzuki, Antimetastatic Effect Of Triton WR 1339, a Nonionic Detergent, On Rat Ascites Tumors, *The Tohoku Journal Of Experimental Medicine*, vol. 128, No. 3, Jul. 1979, pp. 259–265.

(List continued on next page.)

*Primary Examiner*—Robert H. Harrison
*Attorney, Agent, or Firm*—Alston & Bird LLP

[57] ABSTRACT

There is provided novel pharmaceutical compositions containing tyloxapol as the active ingredient. These formulations comprise tyloxapol at concentrations above 0.125%, preferably from about 0.25% to about 5.0%. In addition, the invention encompasses pharmaceutical compositions having reduced hypertonicity which compositions comprise tyloxapol in pharmaceutically acceptable solutions without significant concentrations of hypertonic agents or other active ingredients $NaHCO_3$, or active phospholipids, such as DPPC. The less hypertonic formulations allow one to derive all the benefits of the active ingredient tyloxapol, such as its reduced toxicity and enhanced half-life, while avoiding or reducing side effects, such as bronchospasms, associated with the various hypertonic agents or other active ingredient agents.

9 Claims, 8 Drawing Sheets

U.S. PATENT DOCUMENTS

| | | |
|---|---|---|
| 4,039,669 | 8/1977 | Beyler et al. . |
| 4,826,821 | 5/1989 | Clements .................................. 514/78 |
| 4,944,941 | 7/1990 | Ammann . |
| 5,110,806 | 5/1992 | Clements . |
| 5,134,129 | 7/1992 | Lichtenberger . |
| 5,145,684 | 9/1992 | Liversidge et al. . |
| 5,259,963 | 11/1993 | Wiedemann . |
| 5,362,758 | 11/1994 | Ahmed ................................... 514/777 |
| 5,399,363 | 3/1995 | Liversidge et al. . |
| 5,474,760 | 12/1995 | Ghio et al. . |
| 5,512,270 | 4/1996 | Ghio et al. . |
| 5,576,311 | 11/1996 | Guy . |
| 5,747,001 | 5/1998 | Wiedmann et al. . |
| 5,770,585 | 6/1998 | Kaufman et al. . |
| 5,830,436 | 11/1998 | Ghio et al. ............................... 424/45 |
| 5,840,277 | 11/1998 | Ghio et al. ............................... 424/45 |
| 5,849,263 | 12/1998 | Kennedy ................................. 424/45 |
| 6,024,940 | 2/2000 | Ghio et al. ............................... 424/45 |
| 6,037,328 | 3/2000 | Hu et al. .................................. 514/23 |

OTHER PUBLICATIONS

Robert A. Floyd, Julia J. Watson and Peter K. Wong, Sensitive Assay Of Hydroxyl Free Radical Formation Utilizing High Pressure Liquid Chromatography With Electrochemical Detection Of Phenol And Salicylate Hydroxylation Products, *Journal Of Biochemical And Biophysical Methods*, vol. 10, 1984, pp. 221–235.

Julio F. Turrens, James D. Crapo and Bruce A. Freeman, Protection Against Oxygen Toxicity By Intravenous Injection Of Liposome–Entrapped Catalase And Superoxide Dismutase, *Journal Of Clinical Investigation*, vol. 73, Jan. 1984, pp. 87–95.

Robert A. Floyd, Julia J. Watson and Peter K. Wong, Use Of Salicylate With High Pressure Liquid Chromatography And Electrochemical Detection (LCED) As A Sensitive Measurement Of Hydroxyl Free Radicals In Adriamycin Treated Rats, *Journal Of Free Radicals In Biology & Medicine*, vol. 2, 1986, pp. 13–18.

M.F. McCarty, An Antithrombotic Role For Nutritional Antioxidants: Implications For Tumor Metastasis And Other Pathologies, *Med–Hypotheses*, Apr. 1986, pp. 345–357.

Eiko Kondo and Koomi Kanai, Triton WR–1339 As A Biological–Response Modifier In Mycobacterial Infection, *Japan Journal Medical Science Biology*, vol. 39, 1986, pp. 35–47.

Sadis Matalon, Bruce A. Holm and Robert H. Notter, Mitigation Of Pulmonary Hyperoxic Injury By Administration Of Exogenous Surfactant, *American Physiological Society*, 1987, pp. 756–761.

Robert A. Greenwald, Determination Of HOC1 Production By Micloperoxidase, *CRC Handbook Of Methods For Oxygen Radical Research*, 1987, p. 300.

W.H. Tooley, J.A. Clements, K. Muramatsu, C.L. Brown and M.A. Schlueter, Lung Function In Prematurely Delivered Rabbits Treated With A Synthetic Surfactant, *Am Rev Respir Dis*, Sep. 1987, pp. 651–656.

Robert H. Notter, Biophysical Behavior Of Lung Surfactant: Implications For Respiratory Physiology And Pathophysiology, *Seminars In Perinatology*, vol. 12, No. 3, Jul. 1988, pp. 180–212.

R. Randall Baker, Bruce A. Hom, Peter C. Panus and Sadis Matalon, Development Of $O_2$ Tolerance In Rabbits With No Increase In Antioxidant Enzymes, *American Physiological Society*, 1989, pp. 1679–1684.

Barry Halliwell and John M.C. Gutteridge, Role Of Free Radicals And Catalytic Metal Ions In Human Disease: An Overview, *Methods In Enzymology*, vol. 186, 1990, pp. 1–83.

Michael I. Lethem, Stuart L. James and Christopher Marriott, The Role Of Mucous Glycoproteins In The Rheologic Properties Of Cystic Fibrosis Sputum, *Am Rev Respir Dis*, 1990, pp. 1053–1058.

H. Wiseman, M. Cannon, H.R. Arnstein and D.J. Barlow, The Structural Mimicry Of Membrane Sterols By Tamoxifen: Evidence From Cholesterol Coefficients And Molecular–Modelling For Its Action As A Membrane Anti–Oxidant And An Anti–Cancer Agent, *Biochim–Biophys–Acta.*, Mar. 20, 1992, pp. 197–202.

Andrew J. Ghio, Thomas P. Kennedy, A. Richard Whorton, Alvin L. Crumbliss, Gary E. Hatch and John R. Hoidal, Role Of Surface Complexed Iron In Oxidant Generation And Lung Inflammation Induced By Silicates, *American Journal Of Physiology, Lung Cellular And Molecular Physiology 7*, vol. 263, Jun. 29, 1992, pp. L511–L518.

H. Wiseman, C. Smith, B. Halliwell, M. Cannon, H.R. Arnstein and M.S. Lennard, Droloxifene (3–Hydroxytamoxifen) Has Membrane Antioxidant Ability: Potential Relevance To Its Mechanism Of Therapeutic Actions In Breast Cancer, *Cancer–Lett.*, Sep. 14, 1992, pp. 61–68.

Hong–Suk Kim, Soon–Kyu Chung and Jin Jung, Reevaluation Of The Effect Of Triton X–100 On The Assay Of Superoxide Radical By The Nitrobluetertazolium Reduction Method, *Hanguk Nonghwahak Hoechi (J. Korean Agric. Chem. Soc.)*, 1993, pp. 364–369.

Correspondence from Carolann W. Hootan, Department Of Health & Human Services, regarding Alevaire, dated May 27, 1994, including brochure of Alevaire® dated Nov. 1965.

André Cantin and Donald E. Woods, Protection By Antibiotics Against Myeloperxiodase–Dependent Cytotoxicity To Lung Epithelial Cells In Vitro, *J. Clin. Invest.*, vol. 91, Jan. 1993, pp. 38–45.

Okezie I. Aruoma, Deoxyribose Assay For Detecting Hydroxyl Radicals, *Methods In Enzymology*, vol. 233, 1994, pp. 57–82.

Andrew J. Ghio, Philip J. Fracica, Stephen L. Young and Claude A. Piantadosi, Synthetic Surfactant Scavenges Oxidants And Protects Against Hyperoxic Lung Injury, *Journal Of Applied Physiology*, vol. 77, 1994, pp. 1217–1223.

Carol A. Vasconcellos, Phillip G. Allen, Mary Ellen Wohl, Jeffrey M. Drazen, Paul A. Janmey and Thomas P. Stoesel, Reduction In Viscosity Of Cystic Fibrosis Sputum In Vitro By Gelsolin, *Science*, vol. 263, Feb. 16, 1994, pp. 969–971.

Henry J. Fuchs, M.D., Drucy S. Borowitz, M.D., David H. Christiansen, Dr. P.H., Edward M. Morris, Pharm.D., Martha L. Nash, R.N., Boonie W. Ramsey, M.D., Beryl J. Rosenstein, M.D., Arnold I. Smith, M.D. and Mary Ellen Wohl, M.D., Effect Of Aerosolized Recombinant Human DNase On Exacerbations Of Respiratory Symptoms And On Pulmonary Function In Patients With Cystic Fibrosis, *The New England Journal Of Medicine*, vol. 331, No. 10, Sep. 1994, pp. 637–642.

Bonnie W. Ramsey, M.D., Henry L. Dorrin, M.D., Jay D. Eisenberg, M.D., Ronald L. Gibson, M.D., Ph.D., Evan R. Harwood, M.D., Richard M. Kravitz, M.D., Daniel V. Scridlow, M.D., Robert W. Wilmott, M.D., Susan J. Astley, Ph.D., Mary Ann McBurne, M.S., Kim Wentz, M.D., M.P.H., and Arnold I. Smith, M.D., Efficacy Of Aerosolized Tobramycin In Patients With Cystic Fibrosis, *The New England Journal Of Medicine*, vol. 328, No. 24, pp. 1740–1746.

"Pharmazeutische Stoffliste", 1995, Abdata Pharma–Daten–Service, Eschborn/Taunus XP00203775 "Tyloxapol"—pp. 87–88.

Internal Search Report Application No. PCT/US 97/ 06862.

Rossi, Die Moderne Behandlung Der Mucoviscidose (Zystische Pankreasfibrose), *Deutsche Med. Wochenschr.*, vol. 95, No. 42, pp. 2133–2135, (1970).

Rudnik, Behandlungsergebnisse Von Mucoviszidosekranken Kindern In Einem Sanatorium, *Z. Erkrank. Atm. Org.*, vol. 139, No. 2–3, pp. 117–120, (1974).

Thomassen, Regulation Of Human Alveolar Macrophage Inflammatory Cytokines By Tyloxapol: A Component Of The Synthetic Surfactant Exosurf, *Clin. Immonol. Immunopathol.*, vol. 77, No. 2, pp. 201–205, (Nov. 1995).

Dr. J.W. Cornforth, Dr. P. D'Arcy Hart, R.J.W. Rees and J.A. Stock, Antituberculous effect Of Certain Surface–Active Polyoxyethylene Ethers In Mice, *Nature*, vol. 168, Jul. 28, 1951, pp. 150–153.

Maurice L. Tainter, M.D., Frederick C. Nachod, Ph.D. and Joseph G. Bird, M.D., Alevaire As A Mucolytic Agent, *The New England Journal Of Medicine*, vol. 253, Nov. 3, 1995, pp. 764–767.

K.N.V. Palmer, M.A., M.D. Camb., M.R.C.P., The Effect Of An Aerosol Detergent In Chronic Bronchitis, *The Lancet*, Mar. 23, 1957, pp. 611–613.

John W. Polk, M.D. and Marcelino Medina, M.D., A Comparative Study Of Alevaire And A New Mucolytic Agent, Acumist In Postoperative Patients, *The Eye, Ear, Nose and Throat Monthly*, vol. 49, Jul. 1970, pp. 321–324.

PHARMACEUTICAL COMPOSITIONS CONTAINING ALKYLARYL POLYETHER ALCOHOL POLYMER

CROSS-REFERENCE TO RELATED APPLICATIONS

This application is a divisional of U.S. patent application Ser. No. 08/638,893 filed Apr. 25, 1996, now U.S. Pat. No. 5,849,263 which is a Continuation-in-Part of U.S. application Ser. No. 08/299,316, filed Aug. 31, 1994 now U.S. Pat. No. 5,512,270 and now allowed; which is a Continuation-in-Part of U.S. application Ser. No. 08/039,732, filed Mar. 30, 1993, now abandoned.

BACKGROUND OF THE INVENTION

1. Field of the Invention

The present invention relates to pharmaceutical compositions containing a alkylaryl polyether alcohol polymer. More specifically, the present invention relates to pharmaceutical compositions containing alkylaryl polyether alcohol polymer tyloxapol and to methods for treating respiratory inflammation with the pharmaceutical compositions.

2. The Prior Art

Discussion Of Oxidant-Mediated Injury

Oxygen is life-giving to aerobic plants and animals who depend on it for energy metabolism. It can also be lethal to those same organisms when it is altered from its stable dioxygen ($O_2$) state to any one of three partially reduced species: a) the one electron reduced form superoxide anion ($O_2^-$); b) the two electron reduced form hydrogen peroxide ($H_2O_2$); or the deadly three electron reduced form the hydroxyl radical ($^\cdot OH$). In biologic systems $O_2^-$ and $H_2O_2$ are metabolic byproducts of a host of enzymes (oxygenases) that use oxygen as a cofactor. $H_2O_2$ is also produced from $O_2^-$ by the enzymatic action of superoxide dismutases. However, $^\cdot OH$ is generally produced only when $O_2^-$ and $H_2O_2$ interact with transitional ions of metals such as iron and copper in dangerous cyclical redox reactions:

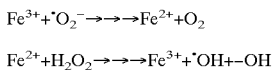

$$Fe^{3+} + {^\cdot}O_2^- \to \to \to Fe^{2+} + O_2$$

$$Fe^{2+} + H_2O_2 \to \to \to Fe^{3+} + {^\cdot}OH + {^-}OH$$

The above reactions are termed the superoxide-driven Fenton reaction common in biological systems. The Fenton reaction can also be initiated by other reducing substances such as ascorbate in the presence of ferric iron and $H_2O_2$.

While $^\cdot O_2^-$ and $H_2O_2$ are each toxic for biological systems, $^\cdot OH$ (and its alternate hypothesized form the ferryl intermediate $FeO^{2+}$) is a highly reactive species that can oxidize unsaturated membrane lipids, damage cellular proteins and cause mutagenic strand breaks in DNA. To prevent injury from partially reduced $O_2$ species under normal conditions, cells have evolved an elaborate system of anti-oxidant enzymes (superoxide dismutase, catalase, glutathione peroxidase) and antioxidant molecules (glutathione, alpha-tocopherol, beta carotene). However, when production of partially reduced $O_2$ species exceeds the capacity of cellular antioxidant defenses to contain them, oxidant injury occurs.

A growing number of mammalian disease entities are now thought to be related to overproduction of partially reduced $O_2$ species, including the reperfusion injury syndromes myocardial infarction and stroke, adult respiratory distress syndrome, oxygen toxicity of the lung, lung injury from asbestos, Parkinson's disease, thermal and solar burns of the skin, and injury to the gastrointestinal tract from nonsteroidal anti-inflammatory agents (see Table IV, page 60, Halliwell B and Gutteridge J M C. *Methods in Enzymology* (1990) 186:1–85). Treatment of these conditions is increasingly directed either toward strategies that prevent enzymatic production of partially reduced $O_2$ species and to the introduction of exogenous antioxidant compounds that restore oxidant-antioxidant balance in biologic and chemical systems. More recently, as will be outlined below, treatment of inflammation in many of these conditions has been directed toward interrupting activation of the transcription factors mediating the genetic expression of pro-inflammatory cytokines important in the pathogenesis of these conditions.

Discussion Of Transcription Factors And Cytokines

Transcription factors are cellular proteins that bind to regulatory sequences of genes and increase or decrease the rate of gene transcription. By affecting the rate of gene transcription, transcription factors play a critical role in regulation of cell function during health and disease. Among the most important transcription factors in disease are those that regulate expression of the genes for pro-inflammatory cytokines. These cytokines are secreted cellular proteins that dramatically affect the behavior of other cells. As examples, the cytokine TNF-α causes weight loss in patients with tumors or chronic infections, produces cellular death and is thought to be an important mediator of septic shock. The cytokine IL-1β mediates fever, and shares many of the properties of TNF. The cytokine IL-8 (and its close relatives such as RANTES) is a potent chemotactic signal aiding in the recruitment of inflammatory cells such as neutrophils. GM-CSF signals the bone marrow to produce more inflammatory cells, activates those cells once produced and lengthens their survival. These cytokines play important roles in mediating the pathogenesis of such inflammatory diseases as cystic fibrosis, chronic bronchitis, asthma and viral infections, among many others (T. L. Bonfield, et al. "Inflammatory cytokines in cystic fibrosis lungs". *American Journal of Respiratory and Critical Care Medicine* (1996) In Press; N. G. McElvaney, et al. "Modulation of airway inflammation in cystic fibrosis. In vivo suppression of interleukin-8 levels on the respiratory epithelial surface by aerosolization of recombinant secretory leukoprotease inhibitor". *Journal of Clinical Investigation* (1992) 90:1296–1301; K. D. Pfeffer, et al. "Expression and regulation of tumor necrosis factor in macrophages from cystic fibrosis patients". *American Journal of Respiratory, Cell and Molecular Biology* (1993) 9:511–519; G. Williams and B. P. Giroir. "Regulation of cytokine gene expression: Tumor necrosis factor, interleukin-1, and the emerging biology of cytokine receptors". *New Horizons* (1995) 3:276–287; C. A. Dinarello. "Role of interleukin-1 and tumor necrosis factor in systemic responses to infection and inflammation". In *Inflammation: Basic Principles and Clinical Correlates*, second edition. J. I Gallin, I. M. Goldstein, and R. Snyderman, editors. Raven Press, Ltd., New York (1992) p. 211–232; W. C. Greene. "The interleukins". In *Inflammation: Basic Principles and Clinical Correlates*, second edition. J. I. Gallin, I. M. Goldstein, and R. Snyderman, editors. Raven Press, Ltd., New York (1992) p. 233–245; M. Baggiolini, et al. "Interleukin-8 and related chemotactic cytokines". In *Inflammation: Basic Principles and Clinical Correlates*, second edition. J. I. Gallin, I. M. Goldstein, and R. Snyderman, editors. Raven Press, Ltd., New York (1992) p. 247–263; D. W. Golde and G. C. Baldwin. "Myeloid growth factors". In *Inflammation: Basic Principles and Clinical Correlates*, second edition. J. I.

Gallin, I. M. Goldstein, and R. Snyderman, editors. Raven Press, Ltd., New York (1992) p. 291–301; R. J. Horwitz and W. W. Busse. "Inflammation and asthma". *Clinics in Chest Medicine* (1995) 16:583–602).

These cytokines share regulation of their expression by the transcription factor Nuclear Factor kappa-B (NF-κB), a particularly important transcription factor mediating inflammatory events (U. Siebenlist, G. Granzuso and R. Brown. "Structure, regulation and function of NF-κB". *Annual Review of Cell Biology* (1994) 10:405–455). NF-κB is also an important transcriptional regulator chemokines such as RANTES (U. Siebenlist, G. Granzuso and R. Brown. "Structure, regulation and function of NF-κB". *Annual Review of Cell Biology* (1994) 10:405–455) and of inducible nitric oxide synthase (iNOS) (P. J. Nelson, et al. "Genomic organisation and transcriptional regulation of the RANTES chemokine gene". *Journal of Immunology* (1993) 151:2601–2612), the enzyme producing nitric oxide (NO), a critical oxidant chemical produced as part of the pathogenesis of septic shock. NF-κB is present in the cytoplasm in an inactive form complexed to an inhibitory protein IκB. A number of events, yet to be completely characterized, cause IκB to dissociate from NF-κB in the cytoplasm. Free NF-κB then localizes to the nucleus, where it binds to a specific κB recognition site in the promoter region of target genes, prompting their expression. NF-κB is activated by a number of stimuli, including cytokines themselves, and by lipopolysaccharide (LPS) (U. Siebenlist, G. Granzuso and R. Brown. "Structure, regulation and function of NF-κB". *Annual Review of Cell Biology* (1994) 10:405–455). NF-κB is also activated by oxidants such as hydrogen peroxide (M. Meyer, R. Schreck, and P. A. Baeverie. "$H_2O_2$ and antioxidants have opposite effects on the activation of NF-κB and AP-1 in intact cells: AP-1 as secondary antioxidant response factor". *EMBO Journal* (1993) 12:2005–2015), suggesting that it may be an oxidant-stress responsive transcription factor. Conversely, some of the most potent inhibitors of NF-κB activation are compounds which can also act as antioxidants. A few, but not most, antioxidants prevent activation of NF-κB by LPS, prevent increases in corresponding messenger RNAs for inflammatory cytokines and decrease levels of TNF and IL-1 in the circulation following LPS injection (E. M. Eugui, et al. "Some antioxidants inhibit, in a coordinate fashion, the production of tumor necrosis factor α, IL-1β and IL-6 by human peripheral blood mononuclear cells". *International Journal of Immunology* (1993) 6:409–422; R. Schreck, et al. "Dithiocarbamates as potent inhibitors of nuclear factor κB activation in intact cells". *Journal of Experimental Medicine* (1992) 175:1181–1194). However, the few antioxidants known to inhibit NF-κB activation share no common structural similarity distinguishing them from those antioxidants that fail to prevent activation of NF-κB (see Eugui, above), preventing one skilled in the art from predicting which antioxidant compounds will and which will not favorably reduce NF-κB activation as a strategy of ameliorating inflammatory events in disease.

Another class of compounds known to inhibit NF-κB activation are anti-inflammatory corticosteroids. Corticosteroids act by combining in the cytoplasm with an intracellular protein called the Glucocorticoid Receptor (GR). Previously, the anti-inflammatory action of corticosteroids was thought to occur exclusively as a result of passage of the GR-steroid complex to the nucleus, where the complex attaches to and influences regulatory gene regions called Glucocorticoid Responsive Elements (GREs). However, recently it has been shown that a major mechanism of anti-inflammatory glucocorticoid activity is inhibition of NF-κB (I. M. Adcock, et al. "Effects of glucocorticoids on transcription factor activation in human peripheral blood mononuclear cells". *American Journal of Physiology* (1995) 268(*Cell Physiology* 37):C331–C338). The GR-steroid complex prevents activation of NF-κB by directly interacting with free NF-κB in the cytoplasm, preventing NF-κB from translocating to the nucleus (A. Ray and K. E. Prefontaine. "Physical association and functional antagonism between the p65 subunit of transcription factor NF-κB and the glucocorticoid receptor". *Proceedings of the National Academy of Sciences, USA* (1994) 91:752–756). However, the GR-steroid complex accomplishes inhibition of NF-κB by mutual repression. By combining with free NF-κB in the cytoplasm, it too is kept from translocating to the nucleus to up-regulate other anti-inflammatory events. Indeed, mutual repression is thought to explain in part the phenomenon of steroid resistance in severe asthmatics. IL-1, IL-6, TNF and other pro-inflammatory cytokines secreted in the airway during an asthma attack increase cellular activation of NF-κB, providing more NF-κB subunits to bind GR-steroid complexes, reducing the amount of GR-steroid complex available to translocate to the nucleus (P. J. Barnes, A. P. Greening and G. K. Crompton. "Glucocorticoid resistance in asthma". *American Journal of Respiratory and Critical Care Medicine* (1995) 152:S125–S142).

Discussion Of Alkylaryl Polyether Alcohol Polymers, Including Tyloxapol

Antioxidants are compounds that can be easily oxidized to stable chemical forms. They can protect chemical and biologic systems by sacrificing themselves to oxidation in preference to oxidation of critically important chemical and biological molecules. Not all oxidizable compounds can perform antioxidant function. To successfully protect chemical and biologic systems from oxidants, the antioxidant must have a higher reactivity for the oxidant than the chemical or biologic molecule which it seeks to protect. To protect the desired chemical and biologic system from oxidation, it is also necessary for the antioxidant to partition itself adjacent to the molecule to be protected. As an example, a molecule to be protected within the lipid bilayer of plasma, endosomal or nuclear membranes might be best protected by an antioxidant with, at least in part, a lipophilic structure, so that it is partitioned to or near the lipid portion of the membrane, adjacent to the molecule needing protection from oxidation.

It has recently been shown that a previously known class of drugs, the alkylaryl polyether alcohol polymers, are potent antioxidants useful in the treatment of mammalian diseases (U.S. Pat. No. 5,474,760 issued 1995 to *Ghio, Kennedy and Piantadosi*, assignors to Duke University, and U.S. Ser. No. 08/039/732). Alkylaryl polyether alcohol polymers are used commercially as surface active detergents and wetting agents (U.S. Pat. No. 2,454,541, issued in 1948 to *Bock and Rainey*, assignors to Rohm & Haas). The best known of this class is tyloxapol, a polymer of 4-(1,1,3,3-tetramethylbutyl)phenol with formaldehyde and oxirane. However, other compounds in the class, sharing the properties of tyloxapol, are well known in the art (J. W. Cornforth, et al. "Antituberculous effect of certain surface-active polyoxyethylene ethers in mice". *Nature* (1951) 168:150–153).

On alkylaryl polyether alcohol polymer used previously in aerosol pharmacologic formulations is tyloxapol, or Triton WR-1339 (M. L. Tainter, et al. "Alevaire as a mucolytic agent". *New England Journal of Medicine* (1955) 253:764–767). A composition sold by Winthrop Laboratories (a division of Sterling Drug, Inc.) and by Breon Laboratories (subsidiary of Sterling Drug, Inc.) under the trademark ALEVAIRE®, containing 0.125% aqueous SUPERINONE® (brand of tyloxapol) in combination with 2% sodium bicarbonate and 5% glycerin, had been marketed for about 30 years for treatment of mucous secretions in patients with diseases and disorders such as chronic bronchitis, croup, pertussis, and poliomyelitis. (See, for example, a product brochure entitled "ALEVAIRE® Detergent Aerosol for Inhalation" (November, 1961) distributed by Breon Laboratories.).

At the time the ALEVAIRE formulation new drug application (NDA) was approved in the early 1950's, the Federal Food, Drug, and Cosmetic Act (FDA Act) did not require FDA to consider efficacy in the drug approval process. In 1962, the FDA Act was amended to require FDA to consider efficacy, and to authorize the agency to remove from the market drugs with approved NDAs if substantial evidence was lacking that the drug was ineffective for its intended use. To comply with the latter legislative mandate, FDA established the Drug Efficacy Study Implementation (DESI) review. ALEVAIRE was considered in the DESI review, and was found to be ineffective. In July of 1968, FDA notified its sponsor, Sterling Drug. Sterling appealed the FDA's findings (*Sterling Drug, Inc., v. Weinberger*, 503F.2d 675 (2d Cir. 1974), 384 F. Supp. 675 (S.D.N.Y. 1974), and 509 F.2d 1236 (2d Cir. 1975)). The legal battle lasted 13 years; it was not until 1981, after a formal evidentiary public hearing, that FDA published an adverse "final decision" on ALEVAIRE that was not appealed by Sterling (ALEVAIRE; Final Decision Following Formal Evidentiary Public Hearing in Adjudicatory Proceeding, 46 Fed. Reg 56043 (Nov. 13, 1981)).

FDA found that there was no evidence that the tyloxapol in ALEVAIRE® had any effect on secretions in the lung from diseases such as chronic bronchitis other than that of water in thinning secretions by simple dilution, and that papers in the manufacturer's bibliography were based on clinical impression and did not reflect adequate controls. (See, letter dated May 27, 1994 to Dr. Thomas Kennedy, one of the co-inventors of the present application, from Ms. Carolann W. Hooton, Chief, Freedom of Information Office, Center for Drug Evaluation and Research, Department of Health & Human Services, Public Health Service, Food and Drug Administration, Rockville, Md.). Surprisingly, the present inventors have found that alkylaryl polyether alcohol polymers of the class typified by tyloxapol, are potent antioxidants, inhibitors of the activation of NF-κB (see Example IV below) and inhibitors of cellular production of pro-inflammatory cytokines (see Example V below).

Even before its withdrawal from the market, there was published evidence that the ALEVAIRE formulation of tyloxapol was associated with side effects in some individuals. Paez and Miller studied ALEVAIRE in 20 patients with chronic obstructive pulmonary disease (Paez, P. N. and W. F. Miller. 1971. Surface active agents in sputum evacuation: a blind comparison with normal saline solution and distilled water. *Chest* 60:312–317). Lung function did not change after subjects inhaled solutions of normal saline, water, or Tergemist (sodium 2-ethylehexyl sulfate 0.125% and potassium iodide 0.1%), but four patients developed evidence of increased airways obstruction after inhaling ALEVAIRE. Subsequently, Fevrier and Bachofen, using a double-blind crossover design, studied the effect of ALEVAIRE or saline as carrier solutions for the inhalation of beta agonists in 24 patients with asthma (Fevrier, D., and H. Bachofen. 1975. Vergleich von tyloxapol (Tacholiquin, ALEVAIRE) mit physiologischer kochsalzlosung als inhalationstragerluscungen. *Schweiz. med Wschr.* 195:810–815). The authors measured specific airway conductance (the inverse of airways resistance) over a 2 hour period following inhalation of 3 ml of test solution. ALEVAIRE solution without beta agonist bronchodilator caused a 20% fall in specific conductance at 20 minutes (p<0.05) that resolved completely by 60 minutes. Thus, the ALEVAIRE formulation was clearly causes bronchospasm after inhalation by susceptible individuals such as those with asthma or airways reactivity.

The present aerosol formulation containing tyloxapol is EXOSURF® NEONATAL, approved by the FDA in 1990 and marketed by Glaxo Welcome as an intratracheally instilled suspension for the treatment of neonatal respiratory distress syndrome. EXOSURF is a formulation of 108 mg diphalmitoylphosphatidyl choine (DPPC), 12 mg cetyl alcohol, 8 mg tyloxapol and 47 mg sodium chloride, reconstituted with 8 ml sterile water. DPPC is thought to be the major functional component. Tyloxapol is added as a dispersing agent so that DPPC can remain an emulsion when reconstituted. When reconstituted, the EXOSURF solution contains 13.5 mg/ml DPPC, 1.5 mg/ml cetyl alcohol, and 1 mg/ml tyloxapol in 0.1 N NaCl. The product is used for both prophylactic and rescue treatment of infants. Neonates treated prophylactically are recommended to receive 3 doses of 5 ml/kg at 12 hour intervals after birth. A number of major adverse effects are seen occasionally seen after EXOSURF administration, including reflux of EXOSURF into the endotracheal tube after intratracheal administration, mucus plugging shortly after administration, pulmonary hemorrhage in low birth weight infants, and arterial oxygen desaturation (EXOSURF Neonatal. 1995. *Physicians Desk Reference.* Medical Economics, Montvale, N.J. 758–762). EXOSURF has also undergone a trial for sepsis-induced adult respiratory distress syndrome in adults (Weg, J. G., R. A. Balk, et al. 1994. Safety and potential efficacy of an aerosollized surfactnat in human sepsis-induced adult respiratory distress syndrome. *J.A.M.A.* 727:1433–1438). Subjects received EXOSURF aerosolized continuously over 12 or 24 hours, respectively for up to 5 days (568.4±53.6 grams in the 12 hour group and 1,128.4±99.3 grams in the 24 hour EXOSURF group). Because of the lipid DPPC component, the aerosol emulsion formulation of EXOSURF tended to accumulate and occlude the exhalation bacterial filter on the mechanical ventilator. One subject suffered a pneumothorax (ruptured lung) as a consequence of this occlusion, when pressure in the ventilator circuit built up and could not escape due to an exhalation valve blocked by the accumulated lipid emulsion.

Synopsis Of Background Discussion

Inflammation in a multitude of diseases is mediated by activation of the transcription factor NF-κB, which in turn causes an increase in cellular production of pro-inflammatory cytokines such as TNF, IL-1, IL-6, IL-8 and the growth factor GM-CSF, and an increase in critical cellular enzymes, such as inducible nitric oxide synthase (iNOS). The current treatment available to prevent activation of NF-κB and subsequent cytokine secretion is anti-inflammatory glucocorticoids. Recently a few, but not most, antioxidants have been found to also inhibit NF-κB.

It is theoretically possible to synthesize a multitude of compounds with antioxidant properties. However, there is no predictable structural similarity among the few agents shown to prevent NF-κB activation. Thus, the demonstration that a compound shows antioxidant activity would not, in of itself, predict that the same compound would also inhibit NF-κB activation and secretion of pro-inflammatory cytokines. Also, the factor limiting use of antioxidants as treatments in biologic systems is the inherent toxicity of many antioxidant compound themselves. Likewise, anti-inflammatory cortosteroids are potent inhibitors of NF-κB, but their use as such is severely limited by the well-known side effects of corticosteroids, including glucose intolerance, hypertension, bone resorption, weight gain and cataracts. Thus, it is a major advantage to discover that a class of commonly used and nontoxic ingredients in medicinal pharmacologic preparations are not only potent antioxidants, but also potent inhibitors of NF-κB activation. Not only can such compounds be used as treatments for diseases where antioxidants might be predicted to be of value, but they can be used as treatments for NF-κB mediated inflammatory conditions without themselves causing toxicity to biologic systems.

The findings presented in the various examples to follow will demonstrate that tyloxapol is a potent antioxidant that also prevents NF-κB activation and suppresses secretion of inflammatory cytokines. These features of tyloxapol would make it a useful anti-inflammatory drug treatment strategy for various mammalian diseases, especially diseases of the respiratory tract. However, the current formulations of tyloxapol, ALEVAIRE and EXOSURF, have undesirable features, such as increasing airways resistance in asthmatics, in the case of ALEVAIRE, or production of plugging of airways and ventilator circuits, in the case of EXOSURF.

SUMMARY OF THE INVENTION

The invention in the present application describes a new formulation of the alkylaryl polyether alcohol polymer tyloxapol. The purpose of this new formulation is to eliminate the undesirable features of the tyloxapol formulations used to date. These features currently limit the therapeutic utility of tyloxapol because of side effects not from tyloxapol but associated with the compositions of the formulations themselves. The present invention describes how alkylaryl polyether alcohol polymers, such as tyloxapol, can be placed in a nontoxic formulation that does not have the undesirable features of previous formulations. Administration of the novel formulations may be similar to those as described in U.S. Pat. Nos. 5,474,760 and 5,512,270 and in U.S. Ser. No. 08/638,893 filed Apr. 25, 1996, (which describe how alkylaryl polyether alcohol polymers are useful as antioxidants in blocking oxidant reactions and biologic injury from partially reduced $O_2$ species, and are useful as treatment agents for inhibiting activation of the transcription factor NF-κB, and as inhibitors of cellular secretion of the cytokines TNF, IL-1, IL-6 and IL-8 and the growth factor GM-CSF), and is repeated below for clarity.

It is the object of the present invention to provide a new formulation of the alkylaryl polyether alcohol polymer tyloxapol for aerosol treatment of respiratory diseases.

It is the further object of the present invention to provide a method to inhibit oxidant chemical reactions caused by partially reduced $O_2$ species.

It is a further object of the present invention to provide a method to protect mammalian tissues against injury from partially reduced $O_2$ species.

It is a further object of the present invention to provide a method and medicament to protect from airway injury by HOCl/OCl, which for convenience, is referred to herein also as HOCl.

It is a further object of the present invention to provide a method for inhibiting oxidant chemical reactions caused by partially reduced $O_2$ species by aerosol treatment with the therapeutic agent.

It is a further object of the present invention to provide a method and medicament for the inhibition of activation of the transcription factor NF-κB (thus ameliorating the pro-inflammatory cellular events evoked by activating genes controlled by this regulatory cell protein).

It is a further object of the present invention to provide a method and medicament for the inhibition of the cytokines TNF, IL-1, IL-6 and IL-8 and the growth factor GM-CSF.

It is a further object of the present invention to provide a method and medicament for preventing glucocorticoid resistance in asthma and other diseases by blocking activation of the transcription factor NF-κB, thereby preventing binding and mutual repression of the glucocorticoid receptor complex by active NF-κB present in the cytoplasm.

It is an advantage of the present invention that the therapeutic agent is formulated to remove injurious ingredients found in previously marketed formulations.

It is an advantage of the present invention that the therapeutic agent is formulated in a higher, more therapeutically effective concentration than previously available.

It is an advantage of the present invention that the therapeutic agent is produced from a toxicologically characterized class of compounds with low toxicologic potential to biologic systems.

The present invention encompasses novel pharmaceutical compositions or formulations comprising tyloxapol as the active ingredient. These formulations comprise tyloxapol at concentrations higher than anything known to the Applicant to have been used in a pharmaceutical formulation previously. As described herein, tyloxapol was previously employed in compositions at concentrations of 0.125%. The pharmaceutical compositions of the present invention comprise concentrations of tyloxapol, or other alkyl aryl polyether alcohol polymers, above 0.125%, preferably from about 0.25% to about 5.0%.

In addition, the invention encompasses pharmaceutical compositions having reduced hypertonicity which compositions comprise tyloxapol in pharmaceutically acceptable solutions without significant concentrations of hypertonic agents or other active ingredients. For example, the formulations having reduced hypertonicity do not contain the hypertonic agents such as $NaHCO_3$, or active phospholipids, such as DPPC, each of which were used in prior formulations. The less hypertonic formulations allow one to derive all the benefits of the active ingredient tyloxapol, such as its reduced toxicity and enhanced half-life, while avoiding or reducing side effects, such as bronchospasms, associated with the various hypertonic agents or other active ingredient agents.

Further, novel formulations of the present invention comprising high concentrations of tyloxapol allow the clinician to more effectively intervene or treat the conditions identified herein. For example, with the higher concentration composition administration is less frequent and more rapid. The high concentration formulations also allow for an aggressive and efficient treatment with excellent distribution within the lung whereas such was not possible with prior formulations which contained tyloxapol.

The compositions or formulations of the present invention can be used for treating a patient afflicted with CF in accordance with the following dosage schedule: once or twice daily at the concentrations described above. It should be recognized that the treating physician or clinician will recognize how to adjust the dose or dosage regimen for a particular patient depending on the severity of the condition or the patient response. Clearly, these novel compositions or formulations containing high concentrations of tyloxapol which are free of $NaHCO_3$, DPPC and significant concentrations of NaCl provide a unique and improved ability to treat CF and other respiratory disorders.

In preferred embodiments of the invention, the medicament is directly instilled into the respiratory system and administered by aerosolization. In this embodiment, the medicament preferably includes a physiologically acceptable carrier which may be selected from the group consisting of physiologically buffered saline, isotonic saline, and normal saline, with the concentration of salt solution adjusted to about 300 mOsm. The pH of the alkylaryl polyether alcohol polymer and carrier mixture is preferably greater than 6.0 but equal to or less than 7.4.

Consideration of the specification, including the several figures and examples to follow, will enable one skilled in the art to determine additional objects and advantages of the invention.

BRIEF DESCRIPTION OF THE DRAWINGS

Reference to the following detailed description may help to better explain the invention in conjunction with the drawings which.

DETAILED DESCRIPTION OF THE INVENTION

Figure 1:
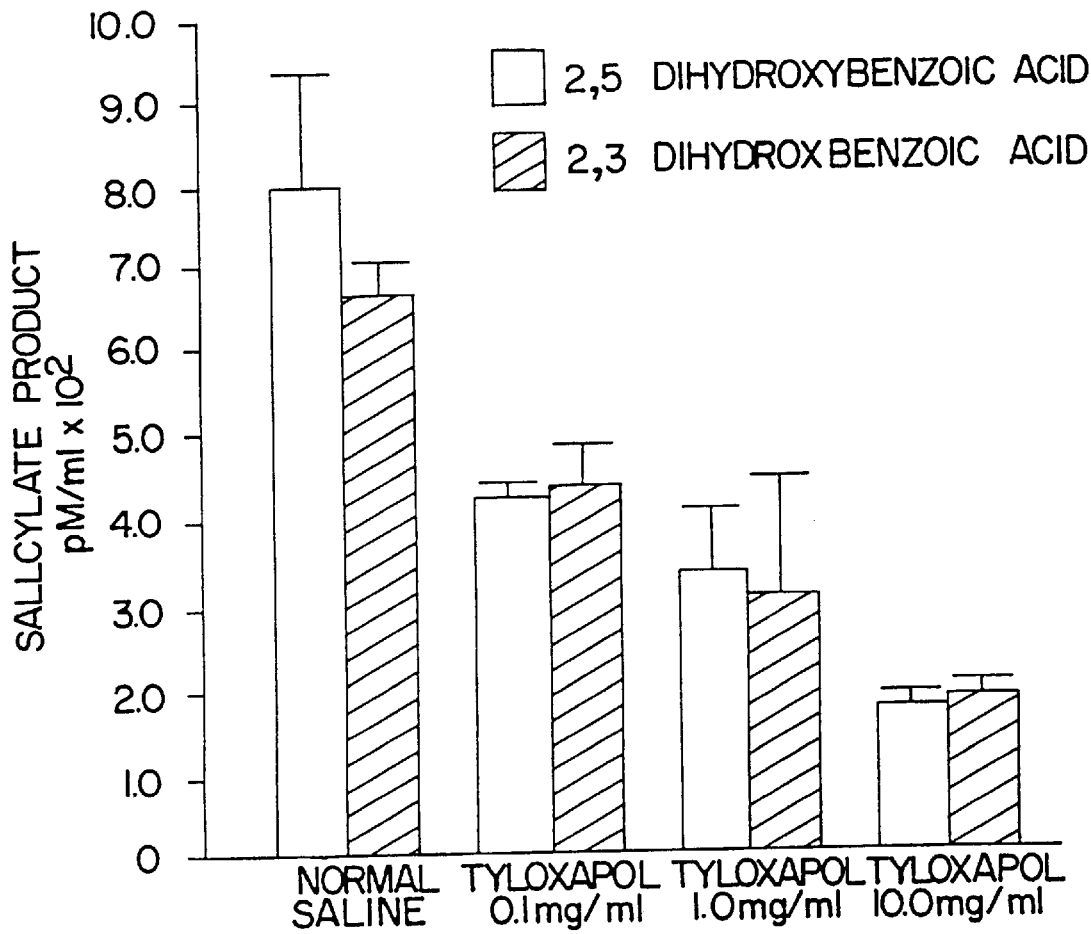
FIG. 1 shows a graph of the inhibitory effect of tyloxapol on ˙OH generation by the Fenton reaction, as measured by hydroxylation of salicylate.

Alkylaryl polyether alcohol polymers can in general be synthesized by condensing alkylaryl alcohols with formaldehyde, as described by Bock and Raney in U.S. Pat. No. 2,454,541 (1948, assigned to Rohm & Haas), the disclosure of which is incorporated herein by reference. The present invention provides a medicament for the inhibition of injurious effects of partially reduced $O_2$ species in chemical and biologic systems comprising a treatment effective amount of alkylaryl polyether alcohol polymer of the formula:

$$\left[ \begin{array}{c} O(RO)yH \\ \phantom{x} \\ \phantom{x} \\ R' \end{array} \right]_x \!\!\!\!\!\! CH_2 \!\!\!\!\!\! \begin{array}{c} O(RO)yH \\ \phantom{x} \\ \phantom{x} \\ R' \end{array}$$

where R=ethylene, R'=$C_4$ to $C_{14}$ straight or branched alkyl, x is greater than 1, and y=2 to 18, effective to inhibit oxidant chemical reactions caused by the oxidant species in the mammal, thereby treating the mammalian disease entities. All alkylaryl polyether alcohol polymers disclosed in this patent should work in the present invention. Several specific alkylaryl polyether alcohol polymers can be easily synthesized by methods previously described (J. W. Conforth, et al. "Antituberculous effect of certain surface-active polyoxyethylene ethers in mice". *Nature* (1951) 168:150–153). The prototype compound of this class, tyloxapol, can be conveniently purchased in pharmacologically acceptable purity from Nycomed, Inc., 33 Riverside Ave., Rensselaer, N.Y. 12144.

Treatment of patients for scavenging partially reduced $O_2$ species and other oxidants, and inhibition of the activation of transcription factor NF-κB and production of the cytokines TNF-α, IL-1β, IL-6, IL-8 and the growth factor GM-CSF with alkylaryl polyether alcohol polymers, particularly tyloxapol, is essentially the same as the administration described in U.S. Pat. Nos. 5,474,760 and 5,512,270.

More specifically, for treatment of mammalian respiratory conditions related to an overproduction of partially reduced $O_2$ species, and for inhibition of the activation of transcription factor NF-κB and production of the cytokines TNF-α, IL-1β, IL-6, IL-8 and the growth factor GM-CSF, the alkylaryl polyether alcohol polymer is dissolved in sterile 0.85 to 0.9% NaCl and water for injection, and the pH is adjusted to approximately 7.0 by addition of NaOH or HCl. Alternately, to stabilize aerosol droplet size and provide a pleasant taste, a 0.1% (v/v) concentration of glycerol can be added to the formulation, and the concentration of NaCl is lowered to 0.8 to 0.85% (w/v) to maintain the formulation within the isotonic range respective to extracellular body fluids (about 300 mOsm). A nonpolymeric alkyl or aryl alcohol such as cetyl alcohol (hexadecanol) may be added equivalent to 1 to 1.5 times the weight of tyloxapol to increase the effectiveness of the mixture in protection against oxidant injury. If cetylc alcohol is added, the concentration of NaCl is decreased proportionally, to provide for a formulation that is isotonic. As an example, the pharmaceutical compositions of the present invention comprise concentrations of tyloxapol or other alkyl aryl polyether alcohol polymers above 0.125%, preferably from about 0.25% to 2.5% (w/v) solution of sterile 0.9% NaCl and water to make an isotonic solution of about 300 mOsm. The concentration of tyloxapol can be increased to from about 2.5% to about 5.0% (w/v) and the isotonicity of the resultant solution can be maintained by decreasing the concentration of NaCl to 0.85%. If 0.1% glycerol is also added, the concentration of NaCl is further decreased to 0.85% for lower concentration solutions and to 0.8% for solutions of higher tyloxapol concentration.

This mixture is then administered to the lung by direct instillation into the respiratory system. The mixture may also be administered by aerosolization using a clinically available positive pressure driven nebulizer that produces respirable particles of less than 5 microns mass median diameter. Jet aerosol nebulizer systems that are useful for the administration of tyloxapol into the airway include the Pari-LC Jet Plus nebulizer (Richmond, Va.), the T-Updraft II Nebumist nebulizer (Hudson, Irvine, Calif.) and the Marquest Acorn II nebulizer (Marquest Medical Products, Inc., Englewood, Co.). Higher concentrations of tyloxapol (0.25 to 5.0%) are favored for aerosolization to deliver an effective drug amount to the airway. Because, tyloxapol has a long half-life of 5–6 days when delivered into the lung (DeAngelis R. L., and J. W. Findlay. 1993. Metabolism of synthetic surfactants. *Clin. Perinatol.* 20:697–710; Sachs, S., and S. L. Young. 1995. Pharmacokinetics of intratracheally instilled tyloxapol in the rat: localization of protection against hyperoxic injury. *Am. J. Respir. Crit. Care Med.* 151:A645), higher concentrations also allow one to deliver tyloxapol as a once a day therapy, thereby leading to greater ease of treatment for the patient and greater patient compliance with prescribed therapy.

As an example, a 0.25 to 5.0% solution of tyloxapol is made in sterile 0.85 to 0.9% NaCl and double glass distilled deionized water to make it isotonic with respect to respiratory secretions. The pH is adjusted to approximately 7.0 to prevent bronchospasm from extremes of acidity or alkalinity. This mixture is sterilized by vacuum filtration through a 0.22 micron Millipore filter and 3.3 ml each is packaged into 5 ml unit dose glass vials with rubber stoppers fastened with aluminum crimp-on "flip-tear" seals. A 0.1% concentration of glycerol may be optionally added to the above mixture to stabilize droplet size during aerosolization, but the concentration of NaCl must be further lowered, as described above.

To enhance the effectiveness of the therapy, a treatment effective amount of a commonly available anti-inflammatory glucocorticoid, such as methylprednisolone (1–5 mg), triamcinolone (1–5 mg), beclomethasone dipropionate (1–4 mg), flunisolide (200–400 µg) or dexamethasone (200–400 µg, either as dexamethasone or its water soluble congener dexamethasone sodium phosphate) may be added to the formulation. Combining an alkylaryl polyether alcohol polymer and an anti-inflammatory glucocorticoid provides a means for reducing glucocorticoid resistance in asthma and other diseases, thereby enhancing glucocorticoid effectiveness. This is accomplished by blocking, with addition of the alkylaryl polyether alcohol polymer, activation of the transcription factor NF-κB, thereby preventing binding and thereby mutual repression of the glucocorticoid receptor complex by active NF-κB present in the cytoplasm. An additional advantage of the combined formulation is that alkylaryl polyether alcohol polymers, as surface active agents, will aid in the solubilization of water-insoluble anti-inflammatory glucocorticoids such as triamcinolone, beclomethasone dipropionate, flunisolide or dexamethasone, thereby promoting their effective distribution to the airway.

For administration of treatment effective doses to the lungs and bronchial airways, 3 ml of sterile tyloxapol solution is inhaled as an aerosol once a day using a clinically available positive pressure driven nebulizer such as the devices described above. Alternately, the mixture can be nebulized into the respiratory delivery circuit of a mechanical ventilatory. A beta sympathetic agonist bronchodilator (such as 1.25 to 2.5 mg of albuterol) can be mixed with the tyloxapol solution and nebulized concomitantly, if desired to decrease total treatment time if the patient is also receiving independent therapy with beta agonist bronchodilators. A quaternary ammonium derivative of atropine such as ipratoprium (500 µg) or glycopyrrolate (200–1,000 µg) can also be added to the tyloxapol solution for the same purpose.

For administration of treatment effective doses to the nasal airway, the sterile tyloxapol solution or tyloxapol solution containing the above anti-inflammatory corticosteroids is placed in a commercially available 10 ml squeeze bottle or similar device that generates a fine mist. For relief of nasal rhinitis, rhinosinusitis or other inflammation, 1 to 4 sprays from this dispense is inhaled into each nostril once or twice a day.

In order to facilitate a further understanding of the invention, the following examples primarily illustrate certain more specific details thereof.

Example I demonstrates the potent activity of alkylaryl polyether alcohol polymers as ˙OH scavengers in chemical systems. Example II demonstrates the therapeutic benefit of using alkylaryl polyether alcohol polymers to prevent mammalian lung injury from exposure to 100% oxygen. Example III demonstrates the potent activity of alkylaryl polyether alcohol polymers as scavengers of HOCl in chemical systems. Example IV demonstrates inhibition of activation of the transcription factor NF-κB. Example V demonstrates suppression of cytokine and GM-CSF production. Example VI demonstrates the extremely hypertonic nature of the original ALEVAIRE formulation and how the formulation described herein solves this problem.

EXAMPLE I
Inhibition Of Oxidants Generated By The Fenton Reaction

The first chemical system used to test the antioxidant activity of alkylaryl polyether alcohol polymers employed salicylate as the target molecule of oxidants. Hydroxyl radical reacts with salicylic acid (2 hydroxybenzoic acid) to produce two dihydroxybenzoic acid products, 2,3- and 2,5-dihydroxybenzoic acid. These hydroxylated products provide evidence of ˙OH generation (R. A. Floyd et al. *Journal of Biochemical and Biophysical Methods* (1984) 10:221–235; R. A. Floyd et al. *Journal of Free Radicals in Biology & Medicine* (1986) 2:13–18).

The detection of 2,3- and 2,5-dihydroxybenzoic acid was performed using high performance liquid chromatography with electrochemical detection. Suspensions of 10 µM $FeCl_3$, 1 mM $H_2O_2$, 1.0 mM ascorbate and 10.0 µM salicyclic acid were employed to generate and detect ˙OH. Either 1.0 ml of normal saline or tyloxapol (final concentrations of 0.0 to 10 mg/ml) were added. The reaction mixtures were incubated at 45° C. for 30 min and centrifuged at 1200 g for 10 min. Supernatant was centrifuged (Beckman Microfuge E) through a 0.22 µM microfuge tube filter (PGC Scientific No. 352-118) at 15,000 g.

A 100 µL sample of the eluate was injected ont a C18 RP HPLC column (250×4.7 mm, Beckman No. 235329). Hydroxylated products of salicylate were quantified with a Coulochem electrochemical detector (ESA model 5100 A) with the detector set at a reducing potential of −0.40 VDC. The guard cell (used as a screen) was set at an oxidizing potential of +0.40 VDC. Measurements were done in duplicate. FIG. 1 shows that the addition of tyloxapol to the reaction mixture inhibited ˙OH generation in a concentration dependent manner.

The second chemical system used to test the antioxidant activity of alkylaryl polyether alcohol polymers employed 2-deoxyribose as the target molecule of oxidants. This pentose sugar reacts with oxidants to yield a mixture of products. On heating with thiobarbituric acid (TBA) at low pH, these products form a pink chromophore that can be measured by its absorbance at 532 nm (B. Halliwell and J. M. C. Gutteridge. *Methods in Enzymology* (1990) 186:1–85).

The chemical system employed to generate oxidants was a reaction mixture containing 10.0 µM $FeCl_3$, 1.0 mM ascorbate, 1.0 mM $H_2O_2$ and 1.0 mM deoxyribose in Hanks Balanced Salt Solution. This system is useful for measuring site-specific ˙OH generation on biologic molecules, as described by Halliwell and Gutteridge in the reference immediately above. Either 0.1 ml of normal saline or tyloxapol (final concentrations of 0.0 to 10.0 mg/mg) were added.

Figure 2:
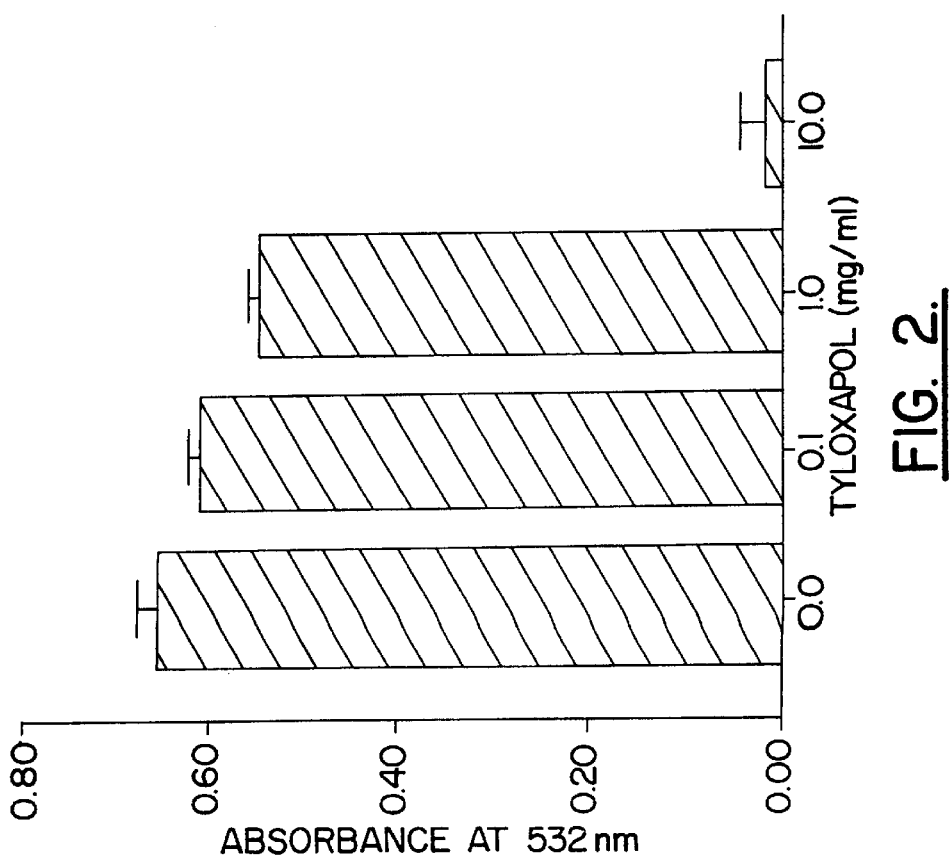
FIG. 2 shows a graph of the inhibitory effect of tyloxapol on ˙OH generation by the Fenton reaction, as measured by oxidation of the sugar, 2-deoxyribose.

The reaction mixtures were incubated at 45° C. for 30 min and centrifuged at 1200 g for 10 min. One ml of both 1.0% (w/v) TBA and 2.8% (w/v) trichloroacetic acid were added to 1.0 ml of supernatant, heated at 100° C. for 10 min, cooled in ice, and the chromophore determined in triplicate by its absorbance at 532 nm. FIG. 2 shows that the addition of 10 mg/ml tyloxapol to the reaction mixture causes marked inhibition of the oxidation of deoxyribose, as measured by absorbance of the oxidant reaction produced at 532 nm.

The third system used to test the antioxidant activity of alkylaryl polyether alcohol polymers employed asbestos as the source of iron for oxidant generation and 2-deoxyribose as the target molecule of oxidants. The generation of oxidants by asbestos has been described previously (A. J. Ghio et al. *American Journal of Physiology* (*Lung Cellular and Molecular Physiology* 7) (1992) 263:L511–L518). The reaction mixture, in a total volume of 2.0 ml phosphate-buffered saline (PBS) contained the following reagents: 1.0 mM deoxyribose, 1.0 mM $H_2O_2$, 1.0 mM ascorbate, and 110 mg/ml crocidolite asbestos. The mixture was incubated at 37° C. for 1 h with agitation and then centrifuged at 1,200 g for 10 min.

Oxidant generation was assessed by measuring TBA reactive products of deoxyribose as detailed in the paragraph above. Measurements were done in triplicate. TABLE I below shows that the addition of tyloxapol inhibited in a concentration dependent manner the generation of oxidants by asbestos, as measured by absorbance of the oxidant reaction product at 532 nm.

TABLE I

Effect of Tyloxapol on Oxidant Generation of Asbestos

| | Absorbance at 532 nm |
|---|---|
| Tyloxapol 0.0 mg/ml | 0.93 ± 0.02 |
| Tyloxapol 0.1 mg/ml | 0.89 ± 0.04 |
| Tyloxapol 1.0 mg/ml | 0.75 ± 0.01 |
| Tyloxapol 10.0 mg/ml | 0.53 ± 0.04 |

EXAMPLE II
Protection From Mammalian Lung Injury By 100% Oxygen

To determine if alkylaryl polyether alcohol polymers could protect against oxidant injury to intact biologic systems, this treatment was studied in a well established model of oxygen toxicity to the lung (J. F. Turrens, et al. *Journal of Clinical Investigation* (1984) 73:87–95). Sixty-day old male Sprague-Dawley rats (Charles River, Inc., Wilmington, Mass.) were tracheally instilled with 0.5 ml of either normal saline, tyloxapol (6.0 mg) or tyloxapol (6.0 mg) and cetyl alcohol (hexadecanol, 11.0 mg). These rats (n=10 in each treatment group) were then exposed to either air or 100% oxygen in plexiglass chambers at a flow rate of 10 liters/min.

Oxygen percentage was monitored by a polarographic electrode and maintained continuously above 98%. Temperature was maintained between 20 and 22° C. Survival times were determined by checking animals every 4 hours. Separate groups of rats treated similarly (n=10 in each treatment group) were exposed to 100% oxygen for 61 hours, and then were euthanized with 100 mg/kg intraperitoneal pentobarbital. Pleural fluid volume was measured by aspirating pleural fluid from the chest cavity through a small incision in the diaphragm. Lung wet/dry weight ratios were calculated from the left lung after drying the tissue for 96 hours at 60° C. Survival data is shown in TABLE II below.

Rats receiving intratracheal tyloxapol had markedly improved survival compared to placebo control animals instilled with saline. The protective effect of tyloxapol was further enhanced by combining it with cetyl alcohol.

TABLE II

Effect of Tyloxapol on Oxygen Toxicity in Rats

| | Percent Survival | | |
|---|---|---|---|
| Hours | Saline | Tyloxapol | Tyloxapol/ Cetyl Alcohol |
| 0 | 100 | 100 | 1 |
| 58 | 100 | 100 | 100 |
| 62 | 83 | 100 | 100 |
| 66 | 42 | 100 | 100 |
| 70 | 17 | 75 | 100 |
| 72 | 17 | 75 | 100 |
| 76 | 8 | 58 | 100 |
| 80 | 8 | 58 | 100 |
| 84 | 8 | 58 | 100 |
| 88 | 8 | 58 | 100 |
| 92 | 0 | 58 | 100 |
| 96 | 0 | 58 | 100 |

Figure 3:
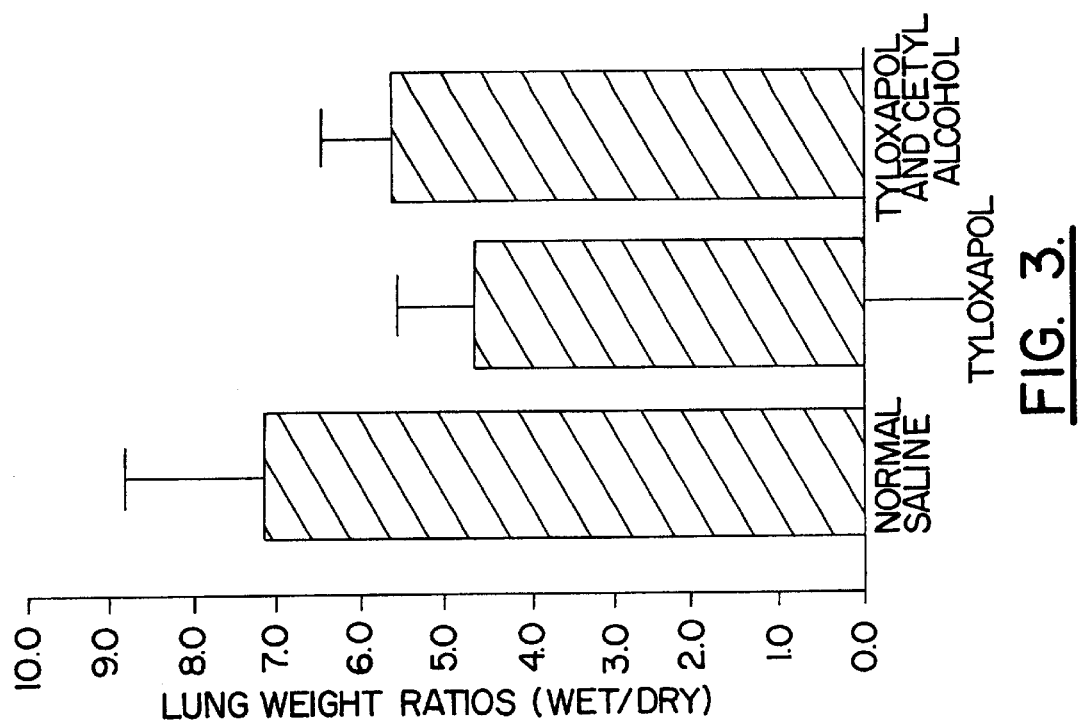
FIG. 3 shows lung wet/dry weight ratios in rats exposed to 100% oxygen and treated with normal saline, tyloxapol, and tyloxapol plus cetyl alcohol.
Figure 4:
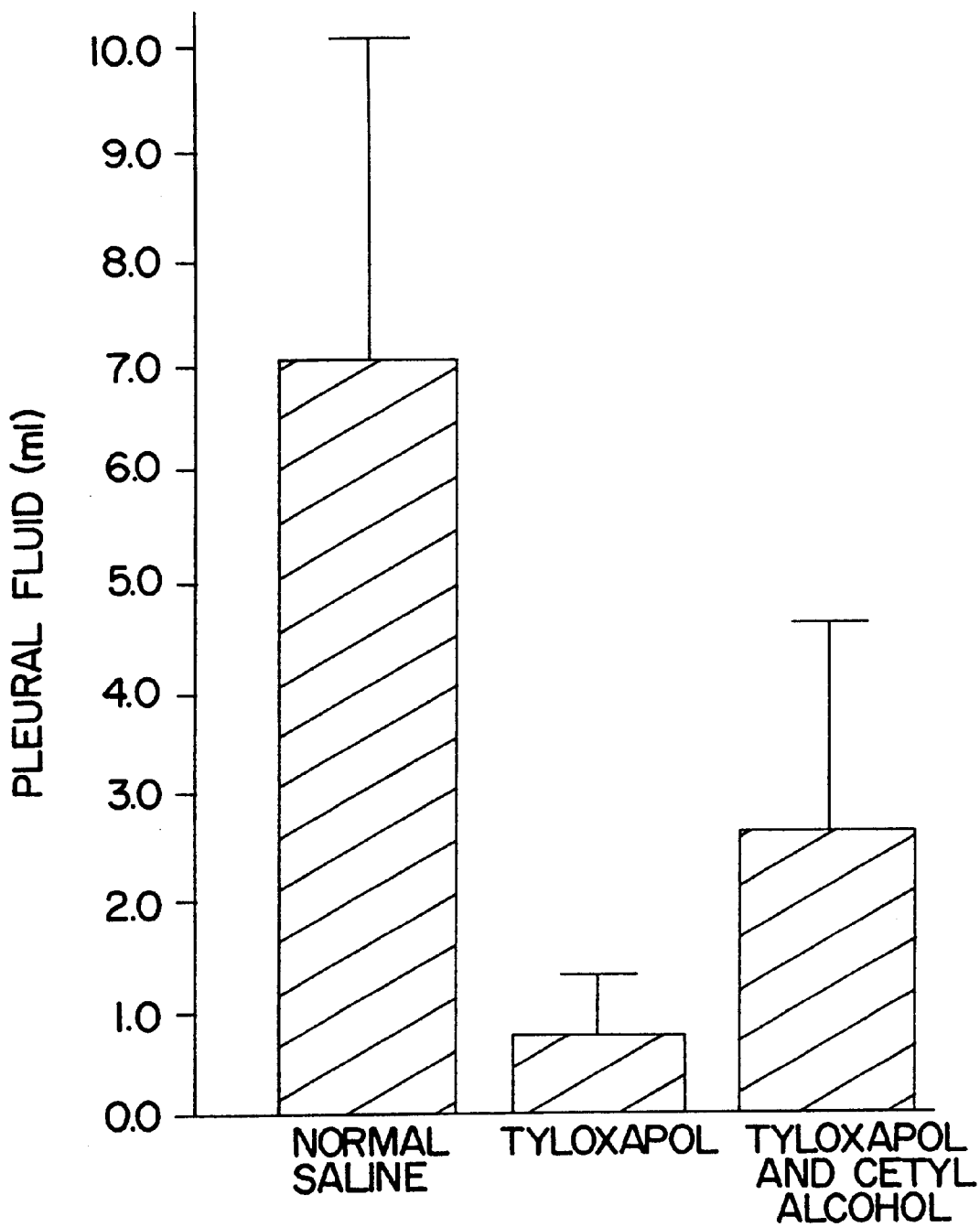
FIG. 4 shows pleural fluid accumulation in rats exposed to 100% oxygen and treated with normal saline, tyloxapol, and tyloxapol plus cetyl alcohol.

Lung wet/dry weight ratios were substantially lower in rats treated with tyloxapol or tyloxapol and cetyl alcohol (FIG. 3), demonstrating that tyloxapol or the combination of tyloxapol and cetyl alcohol protect against edema formation from oxidant injury. Rats treated with tyloxapol or the combination of tyloxapol and cetyl alcohol also had less pleural fluid accumulation than saline treated controls (FIG. 4).

These results demonstrate the ability of alkylaryl polyether alcohol polymers such as tyloxapol to protect against oxidant tissue injury. The survival studies (TABLE II) further demonstrate that the protective effect of the medicament is enhanced by combining it with alcohols such as cetyl alcohol.

EXAMPLE III
Scavenging Of HOCl

The activity of tyloxapol to scavenge OCl⁻ was tested by studying its ability to prevent OCl⁻ mediated oxidant conversion of diethanolamine to its corresponding stable chloramine ("Determination of HOCl Production by Myeloperoxidase", Robert A. Greenwald, editor, *Handbook of Methods for Oxygen Radical Research*, CRC Press, Boca Raton, Fla. (1987), page 300).

The reaction mixture comprised 0.9 ml of 10.0 mM diethanolamine in 0.1 N sodium acetate buffer, pH 4.5. To this was added either 100 µL of 0.1 M NaCl or tyloxapol in 0.1 M NaCl, and the baseline absorbance was read at 280 nm. NaOCl was added to a final concentration of 10 mM.

The reaction mixture was incubated 15 min, and the absorbance was measured at 280 nm. The difference in $A_{280}$ before and after addition of NaOCl was used as a measure of concentration of the stable chloramine. Experiments were performed in triplicate. Results are summarized in Table III below:

TABLE III

Effect of Tyloxapol on HOCl-Induced Choramine Formation

| Microliters of Tyloxapol (10 mg/ml) | Absorbance (Mean ± SD) |
|---|---|
| 0 | 0.505 ± 0.002 |
| 25 | 0.468 ± 0.008 |
| 50 | 0.444 ± 0.023 |
| 75 | 0.377 ± 0.010 |
| 100 | 0.319 ± 0.025 |

To demonstrate that tyloxapol is also an effective scavenger of HOCl in vivo, the ability of tyloxapol to protect against lung injury from HOCl was studied in 60-day old male Sprague-Dawley rats (n=6 per treatment group) weighing 250–300 g (Charles River Breeding Labs, Wilmington, Mass.). After anesthesia with halothane (2–5%) rats were injected intratracheally with either 0.3 ml of 2.0 mM NaOCl in normal saline (buffered to pH 6.0), or with normal saline alone. The rats were allowed to recover, and one hour later were dosed intratracheally with either 6.0 mg tyloxapol in normal saline or with normal saline. Twenty-four hours after NaOCl instillation, all rats were euthanized with sodium pentobarbital. The tracheas were cannulated and lungs were lavaged with normal saline (35 ml/kg body weight). After staining of the lavage fluid with a modified Wright's stain (Diff-Quick stain, ASP, McGraw Park, Ill.), the cell differentials were determined on 500 cells/sample. Values were expressed as the percentage of total cells recovered. Lavage protein was measured using the Bio-Rad method for total protein determination as modified for use on the centrifugal analyzer.

Figure 5A:
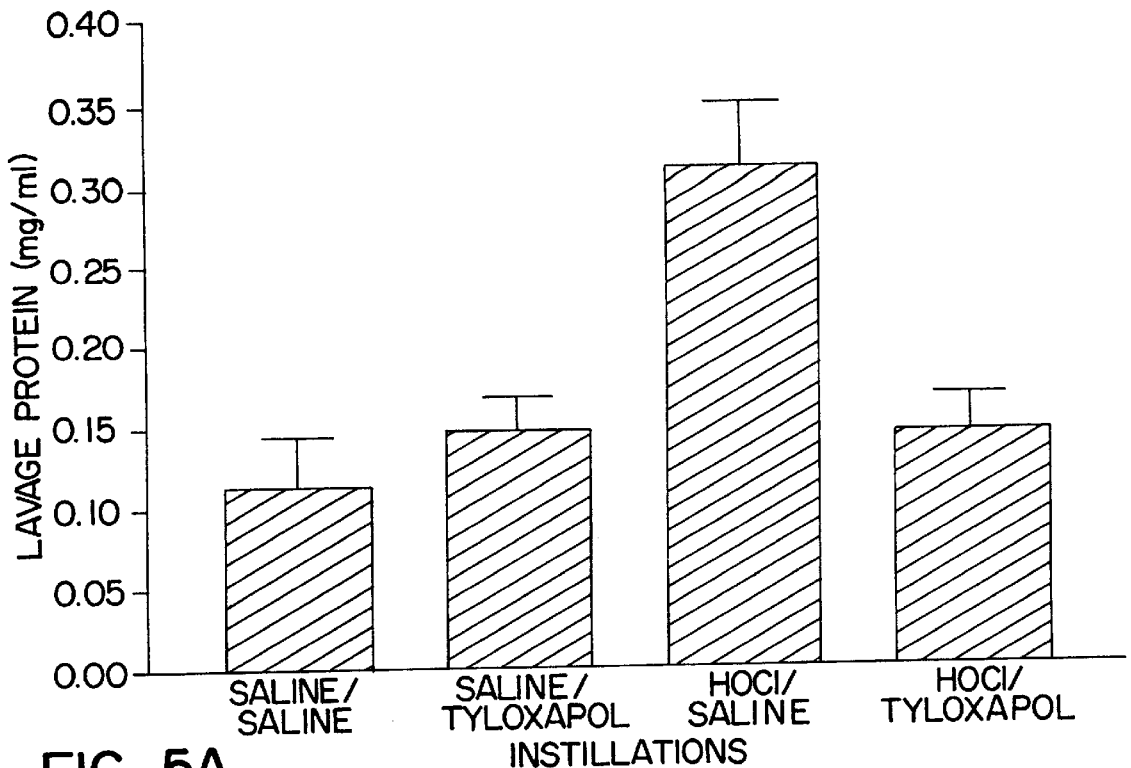
FIGS. 5A and 5B show the effect of tyloxapol on HOCl-mediated lung injury in rats.
Figure 5B:
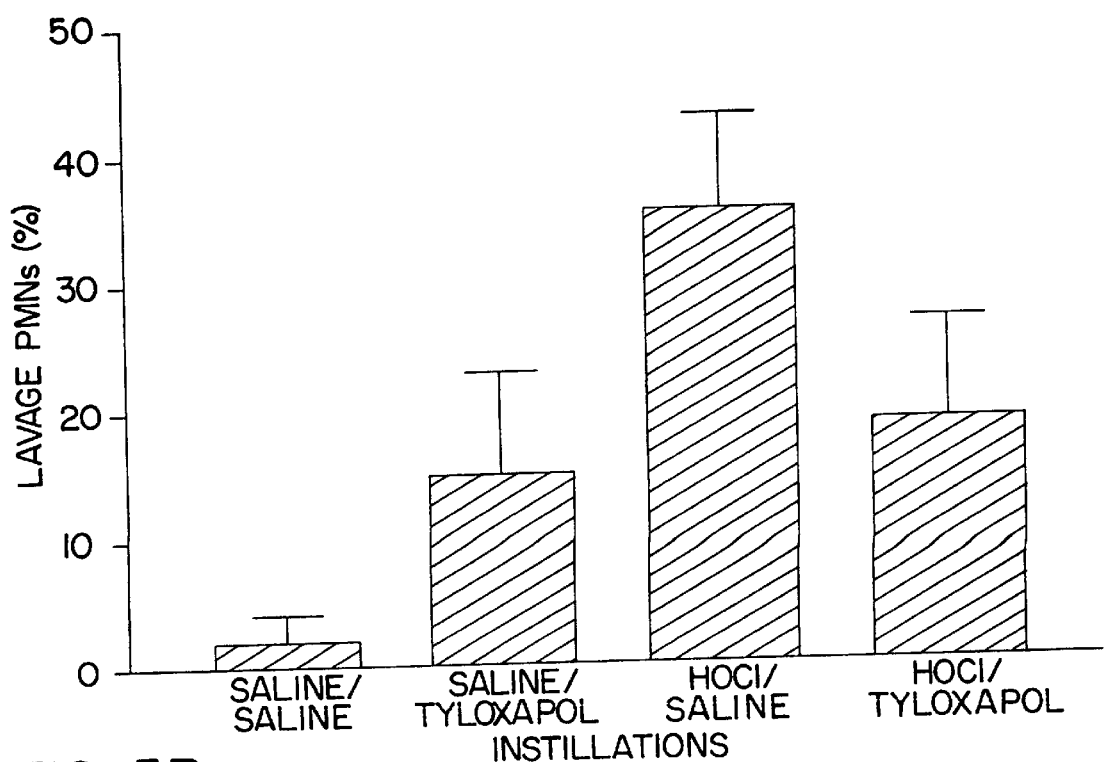

Intratracheal instillation of NaOCl caused acute lung injury as demonstrated by a marked increase in protein concentration and % neutrophils (% PMNs) in lung lavage fluid (FIG. 5). Post exposure treatment with tyloxapol significantly reduced lavage protein concentration (p<0.001) and % PMNs (p<0.01), demonstrating that tyloxapol also protects against HOCl-mediated cytotoxicity in vivo.

Thus, tyloxapol is a potent inhibitor of the oxidant activity of HOCl, and should be useful in preventing HOCl mediated oxidant injury of the airway. Administration of tyloxapol by tracheal instillation to patients with neutrophil-mediated airways diseases such as cystic fibrosis and chronic bronchitis should inhibit HOCl produced in these patients and therefore protect them from oxidant injury. The result should be even better if some cetyl alcohol is admixed with the tyloxapol; preferably, the cetyl alcohol is added in 1 to 1.5 times the weight of the tyloxapol.

Preparation of samples for administration to the patient should be the same as described above in the "DETAILED DESCRIPTION OF THE INVENTION" section herein, most preferably inhalation of 3 ml of a 0.25 to 5.0% isotonic solution of tyloxapol in NaCl and water by jet aerosol once a day.

EXAMPLE IV
Inhibition Of The Activation Of Transcription Factor NF-κB By Tyloxapol As discussed earlier, control of genetic expression of cell proteins is controlled by proteins called transcription factors which bind to regulatory DNA sequences and influence production of the protein product of the regulated gene. An important transcription factor for inflammation is NF-κB, which promotes transcription of the messenger RNA for pro-inflammatory cytokines and growth factors. To determine if tyloxapol inhibits activation of the transcription factor NF-κB, tyloxapol was tested in electrophoretic mobility gel shift assays performed on cultured A549 human lung epithelial cells. A549 human pulmonary epithelial cells were cultured in Ham's F-12 medium supplemented with 10% heat-inactivated fetal calf serum, L-glutamine (2 mM), penicillin (100 U/ml), streptomycin (100 µg/ml) and amphotericin B (250 µg/ml). Confluent cells were stimulated with 10 U/ml IL-1β or 100 µM $H_2O_2$. In some cultures 100 µg/ml tyloxapol was added at the same time as the stimulators. After 2 hours of incubation, nuclear extracts were isolated as described by Dignam et al. (J. D. Dignam, R. M. Lebovita, and R. G. Roeder. "Accurate transcription initiation by RNA polymerase II in a soluble extract from isolated mammalian nuclei" *Nucleic Acid Research* (1983) 11:1475–1489), with minor modifications (C. V. Gunther and B. J. Graves "Identification of ETS domain proteins in murine T lymphocytes that interact with the Moloney murine leukemia virus enhancer" *Molecular and Cellular Biology* (1994) 14:7569–7580). In brief, after removal of the supernatant, cells were scraped gently in 20–30 ml of PBS containing 1 mM phenylmethylsulfonyl fluoride (PMSF) and 1 mM dithiothreitol (DTT). The cell suspension were centrifuged and the pellets were resuspended and incubated for 15 min in 1 ml buffer A containing 10 mM HEPES, 1.5 mM $MgCl_2$, 10 mM KCl, 1 mM PMSF, 1 mM DTT, 10 mM β-glycerolphophate, 2.5 mM benzamidine, 1 mM NaF, 1 mM $NaVO_4$, 1 mg/ml leupeptin and 1 mg/ml pepstatin A, then were sheared by 5 times passage of the suspensions through a 25 G needle. After centrifugation, the pellets were suspended and stirred for 30 min in buffer C containing 25% vol/vol glycerol, 0.25 M NaCl, 1.5 mM $MgCl_2$, 0.2 mM ethylenediamine tetraacetic acid (EDTA), 1 mM PMSF, 1 mM DTT, 10 mM β-glycerolphophate, 2.5 mM benzamidine, 1 mM NaF, 1 mM $NaVO_4$, 1 mg/ml leupeptin and 1 mg/ml pepstatin A. After centrifugation, nuclear extracts were obtained by dialysis of the supernatants in buffer D containing 20 mM HEPES, 20% vol/vol glycerol, 100 mM KCl, 0.2 mM EDTA, 1 mM PMSF and 1 mM DTT. Utilizing the wild type consensus sequences for AP-1 (W. Lee, P. Mitchell and R. Tijan "Purified transcription factor AP-1 interacts with TPA-inducible enhancer elements" *Cell* (1987) 49:742–752) and NF-κB (R. Sen and D. Baltimore. "Multiple nuclear factors interact with the immunoglobulin enhancer sequences" *Cell* (1986) 46:705–716) loci, the following oligonucleotides were synthesized (binding sites underlined):

```
AP-1:    5'-TTCCGGCTGACTCATCAAGCG-3'

3'-AAGGCCGACTGAGTAGTTCGC-5'

NF-κB:   5'-AGTTGAGGGGACTTTCCCAGGC-3'

3'-TCAACTCCCCTGAAAGGGTCCG-5'
```

The oligonucleotides were purified by denaturing polyacrylamide gel electrophoresis followed by passage over Sep-Pak C18 columns. Each complementary strand was end-labeled by phosphorylation with [γ$^{32}$P]-ATP and T4 polynucleotide kinase. Double-stranded DNA probes were generated by annealing the complementary end-labeled oligonucleotide strands, boiling for 3 min and slow-cooling to room temperature in a water bath. Unincorporated radionucleotides were removed by Sephadex G-25 column chromatography. Binding reactions were performed for 20 min on ice with 5–10 µg total protein in a 20 µL volume containing 300 ng bovine serum albumine (BSA), 1–2 µg poly(dI-dC), 50 mM DTT, 0.5 mM PMSF and $1-2\times10^4$ c.p.m. of $^{32}$P-labeled probes. In addition, a concentration of 6 mM $MgCl_2$ was used for AP-1 binding reactions. In selected samples a 100-fold molar excess of unlabeled DNA probe was included in the binding reaction in order to confirm the specificity of DNA-protein interactions. DNA-protein complexes were separated from unbound DNA probe on 4.5% polyacrylamide gels under high ionic strength conditions in 50 mM tris (hydroxymethyl) aminomethane (Tris), 0.4 M glycine, 2 mM EDTA and 2.5% vol/vol glycerol, pH 8.5.

Electrophoresis was carried out at 4° C. at a constant current of 20 mA. Gels were dried under vacuum and exposed to film at −70° C. for 6–24 h with an intensifier screen.

Figure 6:
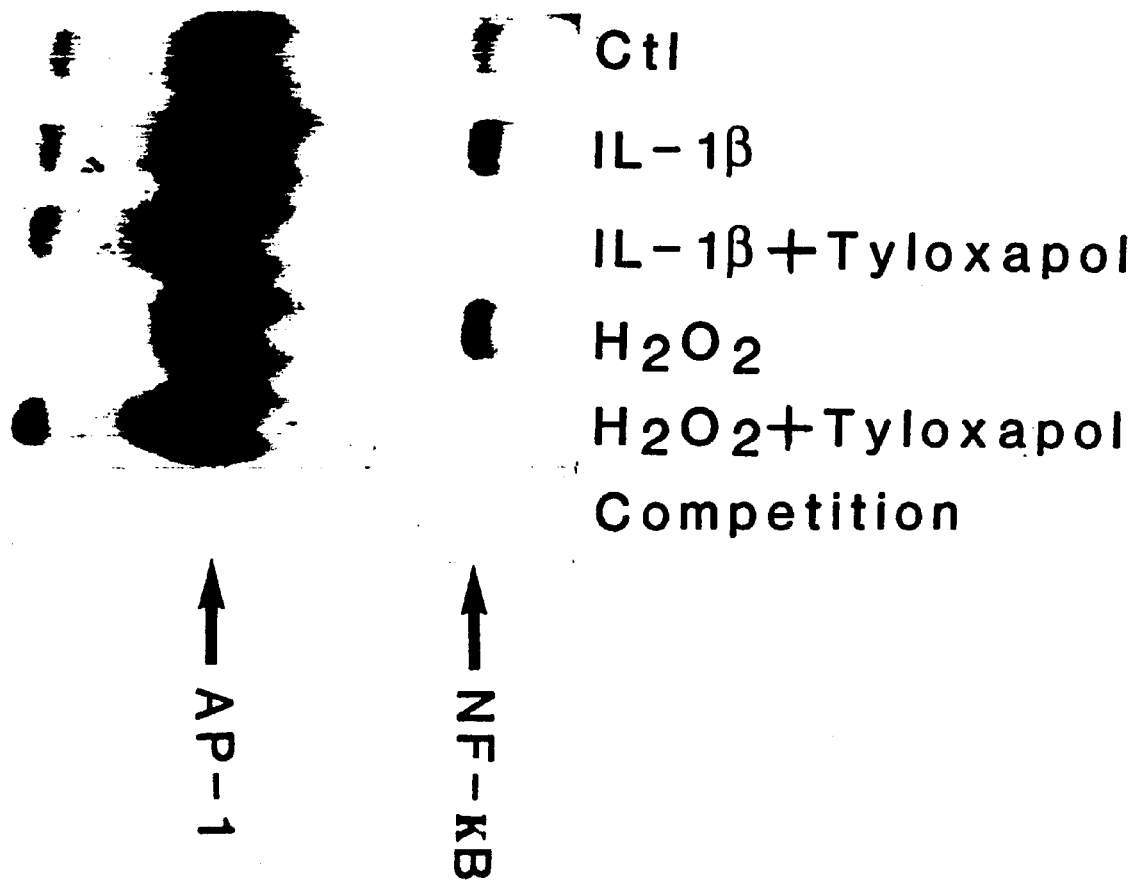
FIG. 6 shows activation of the transcription factor NF-κB by IL-1 and $H_2O_2$ and inhibition of this activation by tyloxapol.

As shown in FIG. 6, tyloxapol prevents IL-1β- or $H_2O_2$-induced binding of NF-κB, but not AP-1, to nuclear extracts. Confluent A549 human pulmonary epithelial cells were incubated without (lane 1) or with 10 U/ml of IL-1β (lanes 2 and 3) or 100 μM $H_2O_2$ (lanes 4 and 5). Tyloxapol (100 ug/ml, lanes 3 and 5) was added at the same time as stimulators. After 3 hours of incubation, nuclear extracts were prepared. Aliquots of the extracts were incubated with $^{32}$P-labeled NF-κB- and AP-1-specific oligonucleotides and analyzed in electrophoretic mobility shift assays as detailed above. Position of the specific DNA-protein complexes are indicated by the arrowhead. One hundred-fold molar excess of the appropriate unlabeled DNA probe was included in the binding reactions for the samples shown in the competition lanes.

Thus, tyloxapol inhibits activation of the transcription factor NF-κB. This action is specific, since the activation of another important transcription factor, AP-1, was not affected. Blocking activation of NF-κB would carry the advantage of reducing cell production of pro-inflammatory cytokines and growth factors, thereby ameliorating inflammation in the tissue treated.

EXAMPLE V
Supression Of Cytokine Production By Tyloxapol

Inhibiting activation of the transcription factor NF-κB would be expected to reduce secretion of the pro-inflammatory cytokines influenced by NF-κB. As examples, cachexia and/or anorexia prominent in patients with severe cystic fibrosis lung disease is caused by an increased rate of TNF gene transcription and secretion by cystic fibrosis macrophages. (See K. D. Pfeffer, et al. "Expression and regulation of tumor necrosis factor in macrophages from cystic fibrosis patients". *American Journal of Respiratory, Cell and Molecular Biology.* (1993) 9:511–519). TNF is also an important mediator in the pathogenesis of asthma (R. J. Horwitz and W. W. Busse. "Inflammation and asthma". *Clinics in Chest Medicine* (1995) 16:585–602). Tyloxapol should ameliorate the adverse effects of TNF in cystic fibrosis and asthmatic pathophysiology when administered to cystic fibrosis or asthmatic patients because, as shown below, it is a potent suppressant of TNF secretion by monocyte-macrophage cell lines. By inhibiting TNF secretion, tyloxapol should also lessen the corticosteroid resistance in asthma caused in part by this cytokine (P. J. Barnes, et al. "Glucocorticoid resistance in asthma". *American Journal of Respiratory and Critical Care Medicine* (1995) 152:S125–S142). Also, IL-8 is a potent chemoattractant for polymorphonuclear neutrophils, and plays a prominent role in the pathogenesis of diverse diseases such as cystic fibrosis, chronic bronchitis, Adult Respiratory Distress Syndrome, and psoriasis (See, H. Nakamura, et al, "Neutrophil elastase in respiratory epithelial lining fluid of individuals with cystic fibrosis induces interluekin-8 gene expression in a human bronchial epithelial cell line". *Journal of Clinical Investigation* (1992) 89:1478–1484; N. G. McElvaney, et al. "Modulation of airway inflammation in cystic fibrosis". In vivo suppression of interleukin-8 levels on the respiratory epithelial surface by aerosolization of recombinant secretory leukoprotease inhibitor. *Journal of Clinical Investigation* (1992) 90:1296–1301; M. Baggiolini, et al. "Interleukin-8 and related chemotactic cytokines". In *Inflammation: Basic Principles and Clinical Correlates*, second edition. J. I. Gallin, I. M. Goldstein, and R. Snyderman, editors. Raven Press, Ltd., New York (1992) p. 247–263). By inhibiting IL-8 secretion, tyloxapol should ameliorate the influx of neutrophils into inflamed tissue in these diseases. Finally, GM-CSF is an important growth factor activating and lengthening the life-span of eosinophils in asthma (D. W. Golde and G. C. Baldwin. "Myeloid growth factors". In *Inflammation: Basic Principles and Clinical Correlates*, second edition. J. I. Gallin, I. M. Goldstein, and R. Snyderman, editors. Raven Press, Ltd., New York (1992) p. 291–301; R. J. Horwitz and W. W. Busse. "Inflammation and asthma". *Clinics in Chest Medicine* (1995) 16:583–602). By reducing GM-CSF secretion, tyloxapol should help reduce the eosinophilia and its consequences for the asthmatic airway.

To test the effect of tyloxapol on cytokine secretion, monocytes were prepared by centrifugal elutriation from leukopaks obtained from healthy human donors. Purified monocytes were suspended at $2\times10^6$ cells in RPMI-1640 supplemented with 100 U/ml penicillin, 100 μg/ml streptomycin, 2 mM L-glutamine, 1 mM sodium pyruvate, 1% MEM non-essential amino acids, 25 mM N-2-hydroxyethyl-ierazine-N'-ethane sulfonic acid (HEPES) and 196 Nutridoma (Boehringer Mannheim, Indianapolis, Ind.), and 5% pooled, heat-inactivated human AB serum (Pelfreeze, Brown Deer, Wis.). One-half ml of this cell suspension was added to each well of a 48-well flat bottomed tissue culture plate. Test materials (diluted in complete medium at 4× the desired final concentration) were added in 250 μL volumes to each well. Control wells received 250 μL of either complete medium or 250 μL of IL-4 (diluted to 4× the desired final concentration of 50 μg/ml). Tyloxapol was tested in triplicate at four concentrations in either the presence or absence of 100 ng/ml *Salmonella typhosa* lipopolysaccharide (LPS, 250 μL of 4× desired final concentration added) and incubated at 37° C. in humidified 5% $CO_2$ for 16 hours. At this time culture supernatants were aspirated off and the unattached cells and cell debris were removed by filtration. The release of TNF-α, IL-1β, IL-6 and IL-8 and the growth factor GM-CSF was determined in the cell-free supernatants using ELISA capture assays. The concentration of endotoxin in all buffers and tyloxapol was below the level of detection (25 pg/ml). Incubations of monocytes in concentrations of tyloxapol equal to or below 100 μg/ml were associated with no significant elevations in LDH concentration in the supernatant, supporting a lack of cytotoxicity by tyloxapol, and suggesting that the inhibition of cytokine secretion noted below was not due to an injurious detergent effect on monocytes.

Figure 7:
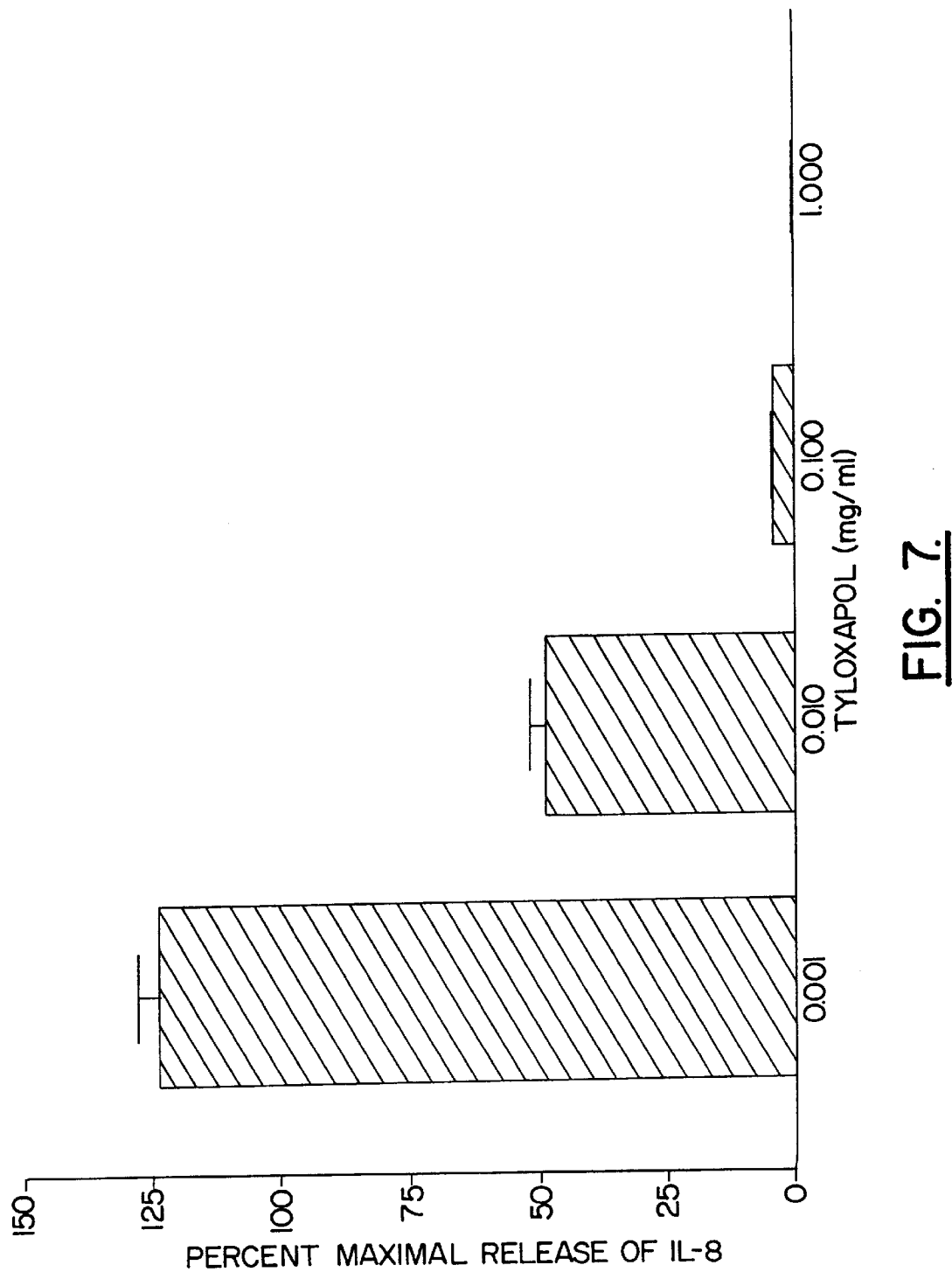
FIG. 7 shows baseline secretion of IL-8 by unstimulated human monocytes with and without tyloxapol treatment.
Figure 8A:
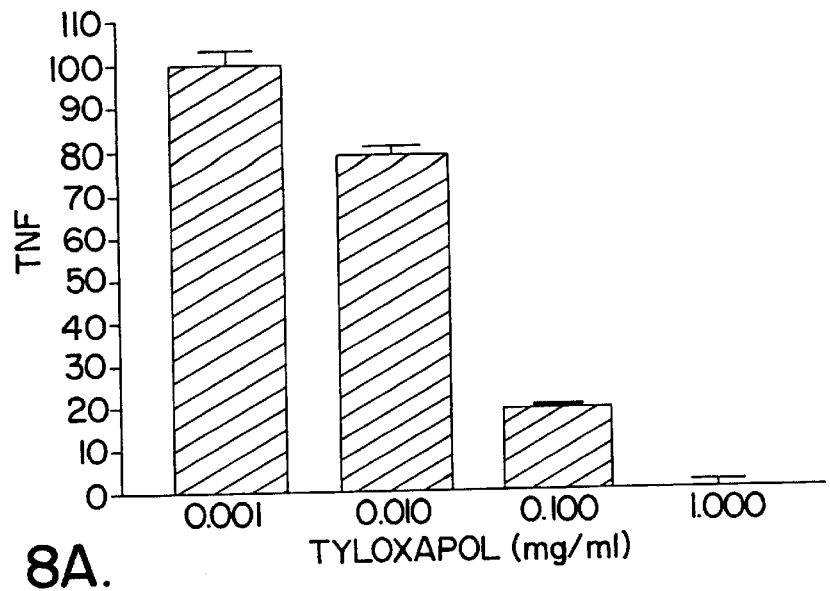
FIG. 8A shows human monocyte secretion of TNF-α with and without tyloxapol treatment.
Figure 8B:
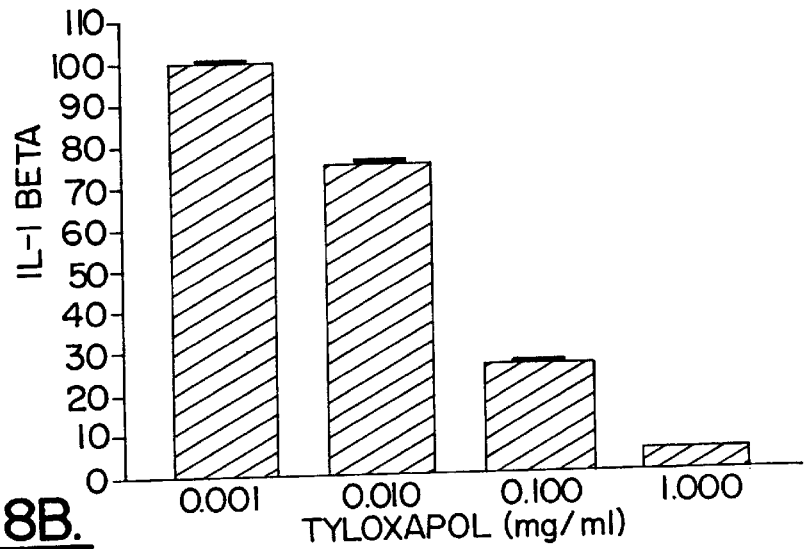
FIG. 8B shows human monocyte secretion of IL-1β with and without tyloxapol treatment.
Figure 8C:
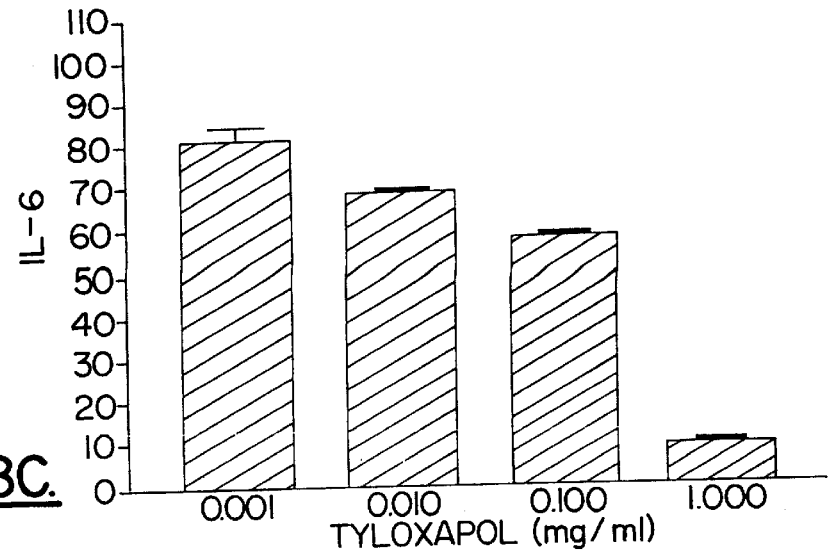
FIG. 8C shows human monocyte secretion of IL-6 with and without tyloxapol treatment.
Figure 8D:
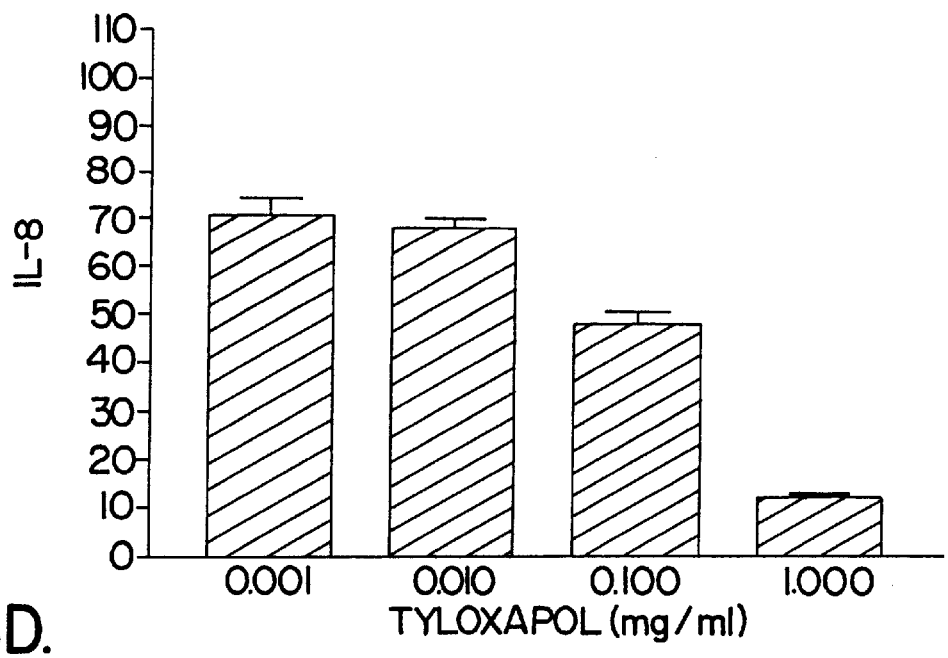
FIG. 8D shows human monocyte secretion of IL-8 with and without tyloxapol treatment.
Figure 8E:
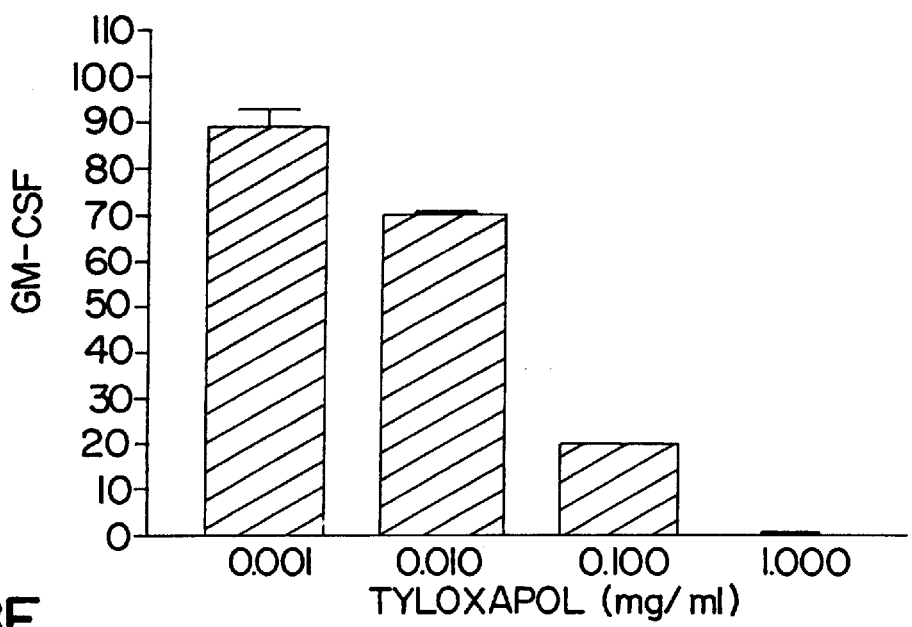
FIG. 8E shows human monocyte secretion of GM-CSF with and without tyloxapol treatment.

Tyloxapol had no effect on baseline release of any mediator except for IL-8, but significantly decreased secretion of IL-8 in unstimulated cells (FIG. 7). However, release of several mediators by LPS stimulated monocytes was significantly diminished at low concentrations of tyloxapol. Secretion of TNF-α, IL-1β, IL-6, IL-8 and GM-CSF was significantly (p<0.01) decreased by tyloxapol in a dose-dependent manner (FIG. 8), with effective concentrations for 50% inhibition ($EC_{50}$ ranging from 30–70 μg/ml (Table IV, below). However, tyloxapol did not change PAF release from LPS stimulated monocytes, providing additional evidence that the effect of tyloxapol was selective on cytokines influenced by NF-κB.

TABLE IV

Effective Concentrations of Tyloxapol for 50% Inhibition $EC_{50}$ of Monocyte Cytokine Release

| Cytokine | $EC_{50}$ (μg/ml) |
|---|---|
| TNF-α | 30 |
| IL-1β | 60 |
| IL-6 | 30 |
| IL-8 | 70 |

Thus, tyloxapol is a potent inhibitor of pro-inflammatory cytokine secretion, a result expected of a therapeutic agent that inhibits the transcription factor NF-κB. As such, tyloxapol would be expected to help ameliorate cachexia and/or anorexia from TNF, such as in patients with cystic fibrosis. Aerosolized tyloxapol would also be expected to reduce airway injury of diseases of airway, such as cystic fibrosis, asthma and chronic bronchitis, and diffuse lung inflammation and injury, such as in Adult Respiratory Distress Syndrome, by inhibiting local production of the chemoatractant IL-8, TNF, IL-1, IL-6 and GM-CSF. Topical tyloxapol would be expected to ameliorate inflammatory diseases of the skin such as psoriasis and response to solar or thermal burn by reducing local production of the same cytokines. The result should be even better if the tyloxapol is mixed in a formulation with glucocorticoids, since by inhibiting NF-κB by a different mechanism than does the glucocorticoid-GR receptor complex, tyloxapol would reduce cytokine-induced-NF-κB related resistance to anti-inflammatory glucocorticoids, as discussed above. Reduction in steroid resistance would, in turn, potentiate the overall anti-inflammatory activity of glucocorticoids and enhance amelioration of inflammation of the body compartment treated. Tyloxapol should also work even better if admixed with some cetyl alcohol, added in 1 to 1.5 times the weight of tyloxapol. Preparation of the samples for administration to the patient should be the same as described above, most preferably inhalation of 3 ml of a 0.25 to 5.0% isotonic solution of tyloxapol in NaCl and water, with or without admixed anti-inflammatory glucocorticoid by jet aerosol once a day.

EXAMPLE VI

The ALEVAIRE formulation of 0.125% tyloxapol, 2% $NaHCO_3$ and 5% glycerol in sterile water was originally devised by Miller as a vehicle for delivery of streptomycin by inhalation to children with tuberculosis (Miller, J. B., H. A. Abramson, and B. Ratner. 1950. Aerosol streptomycin treatment of advanced pulmonary tuberculosis in children. Am. J. Dis. Child. 80:207–237), based on the finding that the combination of sodium bicarbonate and tyloxapol increased susceptibility to streptomycin in vitro. Miller and Boyer then noted a mucolytic effect of the formulation first in a group of adult tuberculosis patients who were reported to have their thick, viscid, difficult-to-expectorate airway secretions become almost immediately thin and watery on therapy with the tyloxapol/glycerol/sodium bicarbonate formulation (Miller, J. B., and E. H. Boyer. 1952. A nontoxic detergent for aerosol use in dissolving viscid bronchopulmonary secretions. J. Pediat. 40:767–771). From this beginning, the formulation of 0.125% tyloxapol, 2% $NaHCO_3$ and 5% glycerol, renamed ALEVAIRE, spread into use as a mucolytic therapy and received an NDA for this use in the early 1950s (Tainter, M. L., F. C. Nachod, and J. G. Bird. 1955. ALEVAIRE as a mucolytic agent. N. Engl. J. Med. 253:764–767). As described earlier, the formulation was withdrawn from the U.S. market in 1981.

Even before its withdrawal from the market, there was published evidence that the ALEVAIRE formulation of tyloxapol was associated with side effects in some individuals. Paez and Miller studied ALEVAIRE in 20 patients with chronic obstructive pulmonary disease (Paez, P. N. and W. F. Miller. 1971. Surface active agents in sputum evacuation: a blind comparison with normal saline solution and distilled water. Chest 60:312–317). Lung function did not change after subjects inhaled solutions of normal saline, water, or Tergemist (sodium 2-ethylehexyl sulfate 0.125% and potassium iodide 0.1%), but four patients developed evidence of increased airways obstruction after inhaling ALEVAIRE. Subsequently, Fevrier and Bachofen, using a double-blind crossover design, studied the effect of ALEVAIRE or saline as carrier solutions for the inhalation of beta agonists in 24 patients with asthma (Fevrier, D., and H. Bachofen. 1975. Vergleich von tyloxapol (Tacholiquin, ALEVAIRE) mit physiologischer kochsalzlosung als inhalationstragerluscungen. Schweiz. med Wschr. 195:810–815). The authors measured specific airway conductance (the inverse of airways resistance) over a 2 hour period following inhalation of 3 ml of test solution. ALEVAIRE solution without beta agonist bronchodilator caused a 20% fall in specific conductance at 20 minutes (p<0.05) that resolved completely by 60 minutes. Thus, the ALEVAIRE formulation was clearly causes bronchospasm after inhalation by susceptible individuals such as those with asthma or airways reactivity.

Hypertonic solutions of sodium chloride cause bronchoconstriction in asthmatic individuals (Kivity, S., J. Greif, et al. 1986. Bronchial inhalation challenge with ultrasonically nebulized saline; comparison to exercise-induced asthma. Ann. Allergy 57:355–358). The inhalation of a solution of 4% sodium chloride or 1% sodium chloride and 18.3% dextrose (1,232 mOsm) can also induce bronchoconstriction (wheezing) in normal subjects (Eschenbacher, W. L., H. A. Boushey, et al. 1983. The effect of osmolarity and ion content of nebulized solutions on cough and bronchoconstriction in human subjects. Am. Rev. Respir. Dis. 1983:127:240). In bronchial rings dissected from fresh human lung tissue, hyperosmolar Krebs-Henseleit buffer (450 mOsm, extra sodium chloride added) evokes a biphasic response: a rapid relaxation phase (peak after 5 min.) followed by a slow contraction phase (peak after 25 min.), with an overall net increase in airway tone to about twice baseline (Jongejan, R. C., J. C. de Jongste, et al. 1991. Effect of hyperosmolarity on human isolated central airways. Br. J. Pharmacol. 102:931–937). The calculated osmolarity of the original ALEVAIRE solution is 1,019 mOsm, not dissimilar from that of the solution found to cause bronchoconstriction in normal subjects (see Eschenbacher, above). Of the total osmolarity, the 2% $NaHCO_3$ contributes by calculation 476 mOsm, the 5% glycerol contributes 548 mOsm and 0.125% tyloxapol contributes only 0.2 mOsm. To confirm this, formulations of 2% $NaHCO_3$ and 5% glycerol in water, with and without 0.125% tyloxapol were made. The osmolarity of these solutions was measured directly by freezing point depression using an Advanced micro-osmometer (Advanced Instruments, Norwood, Mass.). Both solutions, with and without tyloxapol measured approximately 985 mOsm. Thus, tyloxapol, because of its large polymeric nature and size, contributes little to the osmolarity of solution at pharmacologically useful concentrations.

The formulas of the present invention were designed, e.g., to eliminate the hypertonicity of the original Aleviare formulation, in part by using tyloxapol in 0.8 to 0.9% NaCl. To enhance its effectiveness as an antioxidant and anti-inflammatory therapy, tyloxapol concentrations were increased to concentrations above 0.125% to about 0.5% to about 5.0%.

The other aerosol formulation containing tyloxapol is EXOSURF Neonatal (Glaxo-Welcome). When reconstituted in sterile water, EXOSURF contains 13.5 mg/ml DPPC, 1.5 mg/ml cetyl alcohol, and 1 mg/ml tyloxapol in 0.1 N NaCl (a 0.1% solution of tyloxapol). DPPC is eliminated from the formulations of the present invention. It is not necessary for the pharmacologic antioxidant or anti-inflammatory action of tyloxapol, and, as described earlier, is associated with undesired side effects including, but not limited to, mucus plugging of the airways and obstruction of ventilator circuits.

The appended claims set forth various novel and useful features of the invention.

That which is claimed is:

1. A pharmaceutical composition for use in treating respiratory disorders which comprises from 0.25 to 5.0% by weight of tyloxapol and a pharmaceutically acceptable carrier, wherein said composition is adapted for aerosolization into the respiratory tract and has a pH between 6.0 and 7.4 and is isotonic with the airway lining fluid of a subject having a respiratory disorder.

2. The pharmaceutical composition of claim 1 wherein said pharmaceutically acceptable carrier comprises from 0.8 to 0.9% sodium chloride in a buffered or unbuffered solution.

3. The pharmaceutical composition of claim 2 which further comprises 0.1% glycerol.

4. A pharmaceutical composition for use in treating respiratory disorders which comprises from 0.25 to 5.0% by weight of tyloxapol and a pharmaceutically acceptable carrier comprising from 0.8 to 0.9% sodium chloride in a buffered or unbuffered solution having a pH between 6 and 7.4, said composition being adapted for aerosolization into the respiratory tract being substantially free of dipalmitoyl phosphatidyl choline.

5. A pharmaceutical composition for use in treating respiratory disorders which comprises from 0.25% to 5.0% by weight of tyloxapol, from 1 to 1.5 of the concentration of tyloxapol of cetyl alcohol, and a pharmaceutically acceptable carrier, wherein said composition has a pH between 6.0 and 7.4 and is isotonic with the airway lining fluid of a subject having a respiratory disorder and adapted for aerosolization into the respiratory tract, said composition being substantially free of dipalmitoyl phosphatidyl choline.

6. The pharmaceutical composition of claim 5 wherein said pharmaceutically acceptable carrier comprises from 0.8 to 0.9% sodium chloride in a buffered or unbuffered solution.

7. The pharmaceutical composition of claim 5 which further comprises about 0.1% glycerol.

8. The pharmaceutical composition of claim 5 adapted for aerosolization into the respiratory tract, said composition being substantially free of sodium bicarbonate.

9. The pharmaceutical composition of claim 5 adapted for aerosolization into the respiratory tract, said composition being substantially free of dipalmitoyl phosphatidyl choline.

* * * * *